US012721725B2

(12) United States Patent
Dvorsky et al.

(10) Patent No.: US 12,721,725 B2
(45) Date of Patent: Sep. 1, 2026

(54) PROSTHETIC HEART VALVE HAVING NON-LINEAR STRUTS

(71) Applicant: Edwards Lifesciences Corporation, Irvine, CA (US)

(72) Inventors: Anatoly Dvorsky, Haifa (IL); David Maimon, Atlit (IL); Dikla Kersh, Karkur (IL); Gideon Sagi, Kfar Vradim (IL)

(73) Assignee: Edwards Lifesciences Corporation, Irvine, CA (US)

( * ) Notice: Subject to any disclaimer, the term of this patent is extended or adjusted under 35 U.S.C. 154(b) by 912 days.

(21) Appl. No.: 17/750,826

(22) Filed: May 23, 2022

(65) Prior Publication Data

US 2022/0280295 A1 Sep. 8, 2022

Related U.S. Application Data

(63) Continuation of application No. PCT/US2020/063205, filed on Dec. 4, 2020.
(Continued)

(51) Int. Cl.
*A61F 2/24* (2006.01)

(52) U.S. Cl.
CPC .... *A61F 2/2418* (2013.01); *A61F 2220/0041* (2013.01); *A61F 2220/0091* (2013.01);
(Continued)

(58) Field of Classification Search
CPC ............ A61F 2/2418; A61F 2230/0091; A61F 2220/0091; A61F 2220/0041; A61F 2250/001
See application file for complete search history.

(56) References Cited

U.S. PATENT DOCUMENTS 3,409,013 A 11/1968 Berry
3,548,417 A 12/1970 Ronnie et al.
(Continued)

FOREIGN PATENT DOCUMENTS

DE 0144167 C 9/1903
DE 2246526 A1 3/1973
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Suba Ganesan
(74) *Attorney, Agent, or Firm* — Klarquist Sparkman LLP

(57) ABSTRACT

An implantable prosthetic device can include a frame that is radially expandable and compressible between a radially compressed configuration and a radially expanded configuration. The frame can include a plurality of struts, each strut comprising a first portion and a second portion separated by a deflection point. Each strut can be curved helically with respect to a first, longitudinal axis of the frame. The first portion of each strut can be curved in a first direction with respect to a first line parallel to a second axis that is perpendicular to the first, longitudinal axis of the frame, and the second portion of each strut can be curved in a second direction with respect to a second line parallel to the second axis.

17 Claims, 15 Drawing Sheets

Related U.S. Application Data

(60) Provisional application No. 63/094,459, filed on Oct. 21, 2020, provisional application No. 62/945,000, filed on Dec. 6, 2019.

(52) U.S. Cl.
CPC ................ *A61F 2230/0054* (2013.01); *A61F 2230/0067* (2013.01); *A61F 2250/001* (2013.01)

(56) References Cited

U.S. PATENT DOCUMENTS

| | | | |
|---|---|---|---|
| 3,587,115 | A | 6/1971 | Donald |
| 3,657,744 | A | 4/1972 | Ersek |
| 3,671,979 | A | 6/1972 | Moulopoulos |
| 3,714,671 | A | 2/1973 | Edwards et al. |
| 3,755,823 | A | 9/1973 | Hancock |
| 4,035,849 | A | 7/1977 | Angell et al. |
| 4,056,854 | A | 11/1977 | Boretos et al. |
| 4,106,129 | A | 8/1978 | Carpentier et al. |
| 4,222,126 | A | 9/1980 | Boretos et al. |
| 4,265,694 | A | 5/1981 | Boretos et al. |
| 4,297,749 | A | 11/1981 | Davis et al. |
| RE30,912 | E | 4/1982 | Hancock |
| 4,339,831 | A | 7/1982 | Johnson |
| 4,343,048 | A | 8/1982 | Ross et al. |
| 4,345,340 | A | 8/1982 | Rosen |
| 4,373,216 | A | 2/1983 | Klawitter |
| 4,406,022 | A | 9/1983 | Roy |
| 4,441,216 | A | 4/1984 | Ionescu et al. |
| 4,470,157 | A | 9/1984 | Love |
| 4,535,483 | A | 8/1985 | Klawitter et al. |
| 4,574,803 | A | 3/1986 | Storz |
| 4,592,340 | A | 6/1986 | Boyles |
| 4,605,407 | A | 8/1986 | Black et al. |
| 4,612,011 | A | 9/1986 | Kautzky |
| 4,643,732 | A | 2/1987 | Pietsch et al. |
| 4,655,771 | A | 4/1987 | Wallsten |
| 4,692,164 | A | 9/1987 | Dzemeshkevich et al. |
| 4,733,665 | A | 3/1988 | Palmaz |
| 4,759,758 | A | 7/1988 | Gabbay |
| 4,762,128 | A | 8/1988 | Rosenbluth |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,820,299 | A | 4/1989 | Philippe et al. |
| 4,829,990 | A | 5/1989 | Thuroff et al. |
| 4,851,001 | A | 7/1989 | Taheri |
| 4,856,516 | A | 8/1989 | Hillstead |
| 4,878,495 | A | 11/1989 | Grayzel |
| 4,878,906 | A | 11/1989 | Lindemann et al. |
| 4,883,458 | A | 11/1989 | Shiber |
| 4,922,905 | A | 5/1990 | Strecker |
| 4,966,604 | A | 10/1990 | Reiss |
| 4,979,939 | A | 12/1990 | Shiber |
| 4,986,830 | A | 1/1991 | Owens et al. |
| 4,994,077 | A | 2/1991 | Dobben |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,059,177 | A | 10/1991 | Towne et al. |
| 5,080,668 | A | 1/1992 | Bolz et al. |
| 5,085,635 | A | 2/1992 | Cragg |
| 5,089,015 | A | 2/1992 | Ross |
| 5,152,771 | A | 10/1992 | Sabbaghian et al. |
| 5,163,953 | A | 11/1992 | Vince |
| 5,167,628 | A | 12/1992 | Boyles |
| 5,192,297 | A | 3/1993 | Hull |
| 5,266,073 | A | 11/1993 | Wall |
| 5,282,847 | A | 2/1994 | Trescony et al. |
| 5,295,958 | A | 3/1994 | Shturman |
| 5,332,402 | A | 7/1994 | Teitelbaum |
| 5,360,444 | A | 11/1994 | Kusuhara |
| 5,370,685 | A | 12/1994 | Stevens |
| 5,397,351 | A | 3/1995 | Pavcnik et al. |
| 5,411,055 | A | 5/1995 | Kane |
| 5,411,552 | A | 5/1995 | Andersen et al. |
| 5,443,446 | A | 8/1995 | Shturman |
| 5,480,424 | A | 1/1996 | Cox |
| 5,500,014 | A | 3/1996 | Quijano et al. |
| 5,545,209 | A | 8/1996 | Roberts et al. |
| 5,545,214 | A | 8/1996 | Stevens |
| 5,549,665 | A | 8/1996 | Vesely et al. |
| 5,554,185 | A | 9/1996 | Block et al. |
| 5,558,644 | A | 9/1996 | Boyd et al. |
| 5,571,175 | A | 11/1996 | Vanney et al. |
| 5,584,803 | A | 12/1996 | Stevens et al. |
| 5,591,185 | A | 1/1997 | Kilmer et al. |
| 5,591,195 | A | 1/1997 | Taheri et al. |
| 5,607,464 | A | 3/1997 | Trescony et al. |
| 5,609,626 | A | 3/1997 | Quijano et al. |
| 5,628,792 | A | 5/1997 | Lentell |
| 5,639,274 | A | 6/1997 | Fischell et al. |
| 5,665,115 | A | 9/1997 | Cragg |
| 5,716,417 | A | 2/1998 | Girard et al. |
| 5,728,068 | A | 3/1998 | Leone et al. |
| 5,749,890 | A | 5/1998 | Shaknovich |
| 5,756,476 | A | 5/1998 | Epstein et al. |
| 5,769,812 | A | 6/1998 | Stevens et al. |
| 5,800,508 | A | 9/1998 | Goicoechea et al. |
| 5,840,081 | A | 11/1998 | Andersen et al. |
| 5,855,597 | A | 1/1999 | Jayaraman |
| 5,855,601 | A | 1/1999 | Bessler et al. |
| 5,855,602 | A | 1/1999 | Angell |
| 5,925,063 | A | 7/1999 | Khosravi |
| 5,957,949 | A | 9/1999 | Leonhardt et al. |
| 6,027,525 | A | 2/2000 | Suh et al. |
| 6,132,473 | A | 10/2000 | Williams et al. |
| 6,168,614 | B1 | 1/2001 | Andersen et al. |
| 6,171,335 | B1 | 1/2001 | Wheatley et al. |
| 6,174,327 | B1 | 1/2001 | Mertens et al. |
| 6,210,408 | B1 | 4/2001 | Chandrasekaran et al. |
| 6,217,585 | B1 | 4/2001 | Houser et al. |
| 6,221,091 | B1 | 4/2001 | Khosravi |
| 6,231,602 | B1 | 5/2001 | Carpentier et al. |
| 6,245,102 | B1 | 6/2001 | Jayaraman |
| 6,299,637 | B1 | 10/2001 | Shaolian et al. |
| 6,302,906 | B1 | 10/2001 | Goicoechea et al. |
| 6,338,740 | B1 | 1/2002 | Carpentier |
| 6,350,277 | B1 | 2/2002 | Kocur |
| 6,352,547 | B1 | 3/2002 | Brown et al. |
| 6,425,916 | B1 | 7/2002 | Garrison et al. |
| 6,440,764 | B1 | 8/2002 | Focht et al. |
| 6,454,799 | B1 | 9/2002 | Schreck |
| 6,458,153 | B1 | 10/2002 | Bailey et al. |
| 6,461,382 | B1 | 10/2002 | Cao |
| 6,468,660 | B2 | 10/2002 | Ogle et al. |
| 6,482,228 | B1 | 11/2002 | Norred |
| 6,488,704 | B1 | 12/2002 | Connelly et al. |
| 6,506,211 | B1 * | 1/2003 | Skubitz .................. A61F 2/915 623/1.15 |
| 6,527,979 | B2 | 3/2003 | Constantz et al. |
| 6,569,196 | B1 | 5/2003 | Vesely |
| 6,582,462 | B1 | 6/2003 | Andersen et al. |
| 6,605,112 | B1 | 8/2003 | Moll et al. |
| 6,652,578 | B2 | 11/2003 | Bailey et al. |
| 6,689,123 | B2 | 2/2004 | Pinchasik |
| 6,716,244 | B2 | 4/2004 | Klaco |
| 6,730,118 | B2 | 5/2004 | Spenser et al. |
| 6,733,525 | B2 | 5/2004 | Yang et al. |
| 6,767,362 | B2 | 7/2004 | Schreck |
| 6,769,161 | B2 | 8/2004 | Brown et al. |
| 6,783,542 | B2 | 8/2004 | Eidenschink |
| 6,830,584 | B1 | 12/2004 | Seguin |
| 6,878,162 | B2 | 4/2005 | Bales et al. |
| 6,893,460 | B2 | 5/2005 | Spenser et al. |
| 6,908,481 | B2 | 6/2005 | Cribier |
| 6,936,067 | B2 | 8/2005 | Buchanan |
| 7,018,406 | B2 | 3/2006 | Seguin et al. |
| 7,018,408 | B2 | 3/2006 | Bailey et al. |

(56) References Cited

U.S. PATENT DOCUMENTS 7,096,554 B2 8/2006 Austin et al.
7,225,518 B2 6/2007 Eidenschink et al.
7,276,078 B2 10/2007 Spenser et al.
7,276,084 B2 10/2007 Yang et al.
7,316,710 B1 1/2008 Cheng et al.
7,318,278 B2 1/2008 Zhang et al.
7,374,571 B2 5/2008 Pease et al.
7,393,360 B2 7/2008 Spenser et al.
7,462,191 B2 12/2008 Spenser et al.
7,510,575 B2 3/2009 Spenser et al.
7,563,280 B2 7/2009 Anderson et al.
7,585,321 B2 9/2009 Cribier
7,618,446 B2 11/2009 Andersen et al.
7,618,447 B2 11/2009 Case et al.
7,655,034 B2 2/2010 Mitchell et al.
7,785,366 B2 8/2010 Maurer et al.
7,959,665 B2 6/2011 Pienknagura
7,959,672 B2 6/2011 Salahieh et al.
7,993,394 B2 8/2011 Hariton et al.
8,029,556 B2 10/2011 Rowe
8,075,611 B2 12/2011 Millwee et al.
8,128,686 B2 3/2012 Paul et al.
8,167,932 B2 5/2012 Bourang et al.
8,291,570 B2 10/2012 Eidenschink et al.
8,348,998 B2 1/2013 Pintor et al.
8,449,606 B2 5/2013 Eliasen et al.
8,454,685 B2 6/2013 Hariton et al.
8,652,203 B2 2/2014 Quadri et al.
8,685,055 B2 4/2014 VanTassel et al.
8,747,463 B2 6/2014 Fogarty et al.
9,078,781 B2 7/2015 Ryan et al.
11,224,509 B2 1/2022 Dasi et al.
2001/0021872 A1 9/2001 Bailey et al.
2002/0026094 A1 2/2002 Roth
2002/0032481 A1 3/2002 Gabbay
2002/0138135 A1 9/2002 Duerig et al.
2002/0143390 A1 10/2002 Ishii
2002/0173842 A1 11/2002 Buchanan
2003/0014105 A1 1/2003 Cao
2003/0040791 A1 2/2003 Oktay
2003/0050694 A1 3/2003 Yang et al.
2003/0100939 A1 5/2003 Yodfat et al.
2003/0158597 A1 8/2003 Quiachon et al.
2003/0212454 A1 11/2003 Scott et al.
2004/0024452 A1 2/2004 Kruse et al.
2004/0039436 A1 2/2004 Spenser et al.
2004/0078074 A1 4/2004 Anderson et al.
2004/0186558 A1 9/2004 Pavcnik et al.
2004/0186563 A1 9/2004 Lobbi
2004/0186565 A1 9/2004 Schreck
2004/0260389 A1 12/2004 Case et al.
2005/0010285 A1 1/2005 Lambrecht et al.
2005/0075725 A1 4/2005 Rowe
2005/0075728 A1 4/2005 Nguyen et al.
2005/0096736 A1 5/2005 Osse et al.
2005/0096738 A1 5/2005 Cali et al.
2005/0137686 A1 6/2005 Salahieh et al.
2005/0188525 A1 9/2005 Weber et al.
2005/0203614 A1 9/2005 Forster et al.
2005/0203617 A1 9/2005 Forster et al.
2005/0234546 A1 10/2005 Nugent et al.
2006/0004469 A1 1/2006 Sokel
2006/0025857 A1 2/2006 Bergheim et al.
2006/0058872 A1 3/2006 Salahieh et al.
2006/0074484 A1 4/2006 Huber
2006/0108090 A1 5/2006 Ederer et al.
2006/0149350 A1 7/2006 Patel et al.
2006/0183383 A1 8/2006 Asmus et al.
2006/0229719 A1 10/2006 Marquez et al.
2006/0259136 A1 11/2006 Nguyen et al.
2006/0259137 A1 11/2006 Artof et al.
2006/0287717 A1 12/2006 Rowe et al.
2007/0005131 A1 1/2007 Taylor
2007/0010876 A1 1/2007 Salahieh et al.
2007/0010877 A1 1/2007 Salahieh et al.
2007/0112422 A1 5/2007 Dehdashtian
2007/0162102 A1 7/2007 Ryan et al.
2007/0203503 A1 8/2007 Salahieh et al.
2007/0203575 A1 8/2007 Forster et al.
2007/0203576 A1 8/2007 Lee et al.
2007/0208550 A1 9/2007 Cao et al.
2007/0213813 A1 9/2007 Segesser et al.
2007/0233228 A1 10/2007 Eberhardt et al.
2007/0260305 A1 11/2007 Drews et al.
2007/0265700 A1 11/2007 Eliasen et al.
2008/0021546 A1 1/2008 Patz et al.
2008/0114442 A1 5/2008 Mitchell et al.
2008/0125853 A1 5/2008 Bailey et al.
2008/0154355 A1 6/2008 Benichou et al.
2008/0183271 A1 7/2008 Frawley et al.
2008/0208327 A1 8/2008 Rowe
2008/0243245 A1 10/2008 Thambar et al.
2008/0255660 A1 10/2008 Guyenot et al.
2008/0275537 A1 11/2008 Limon
2008/0294248 A1 11/2008 Yang et al.
2009/0118826 A1 5/2009 Khaghani
2009/0125118 A1 5/2009 Gong
2009/0157175 A1 6/2009 Benichou
2009/0276040 A1 11/2009 Rowe et al.
2009/0281619 A1 11/2009 Le et al.
2009/0287296 A1 11/2009 Manasse
2009/0287299 A1 11/2009 Tabor et al.
2009/0299452 A1 12/2009 Eidenschink et al.
2009/0319037 A1 12/2009 Rowe et al.
2010/0004735 A1 1/2010 Yang et al.
2010/0049313 A1 2/2010 Alon et al.
2010/0082094 A1 4/2010 Quadri et al.
2010/0100176 A1 4/2010 Elizondo et al.
2010/0168844 A1 7/2010 Toomes et al.
2010/0185277 A1 7/2010 Braido et al.
2010/0198347 A1 8/2010 Zakay et al.
2010/0204781 A1 8/2010 Alkhatib
2011/0015729 A1 1/2011 Jimenez et al.
2011/0022157 A1 1/2011 Essinger et al.
2011/0066224 A1 3/2011 White
2011/0137397 A1 6/2011 Chau et al.
2011/0218619 A1 9/2011 Benichou et al.
2011/0319991 A1 12/2011 Hariton et al.
2012/0030090 A1 2/2012 Johnston et al.
2012/0089223 A1 4/2012 Nguyen et al.
2012/0101571 A1 4/2012 Thambar et al.
2012/0123529 A1 5/2012 Levi et al.
2012/0259409 A1 10/2012 Nguyen et al.
2013/0023985 A1 1/2013 Khairkhahan et al.
2013/0046373 A1 2/2013 Cartledge et al.
2013/0150956 A1 6/2013 Yohanan et al.
2013/0166017 A1 6/2013 Cartledge et al.
2013/0190857 A1 7/2013 Mitra et al.
2013/0274873 A1 10/2013 Delaloye et al.
2013/0310926 A1 11/2013 Hariton
2013/0317598 A1 11/2013 Rowe et al.
2013/0331929 A1 12/2013 Mitra et al.
2014/0194981 A1 7/2014 Menk et al.
2014/0200661 A1 7/2014 Pintor et al.
2014/0209238 A1 7/2014 Bonyuet et al.
2014/0222136 A1 8/2014 Geist et al.
2014/0277417 A1 9/2014 Schraut et al.
2014/0277419 A1 9/2014 Garde et al.
2014/0277424 A1 9/2014 Oslund
2014/0277563 A1* 9/2014 White .................. A61F 2/2418
623/23.7
2014/0296962 A1 10/2014 Cartledge et al.
2014/0330372 A1 11/2014 Weston et al.
2014/0343670 A1 11/2014 Bakis et al.
2014/0343671 A1 11/2014 Yohanan et al.
2014/0350667 A1 11/2014 Braido et al.
2015/0073545 A1 3/2015 Braido
2015/0073546 A1 3/2015 Braido
2015/0135506 A1 5/2015 White
2015/0157455 A1 6/2015 Hoang et al.
2016/0045306 A1* 2/2016 Agrawal ............... A61F 2/2418
623/2.38
2016/0374802 A1 12/2016 Levi et al.
2017/0014229 A1 1/2017 Nguyen-Thien-Nhon et al.

(56) References Cited

U.S. PATENT DOCUMENTS

| | | | |
|---|---|---|---|
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |
| 2019/0159894 A1 | 5/2019 | Levi et al. |
| 2019/0192288 A1 | 6/2019 | Levi et al. |
| 2019/0192289 A1 | 6/2019 | Levi et al. |
| 2019/0328518 A1 | 10/2019 | Neumann |

FOREIGN PATENT DOCUMENTS

| | | | |
|---|---|---|---|
| DE | 19532846 | A1 | 3/1997 |
| DE | 19546692 | A1 | 6/1997 |
| DE | 19857887 | A1 | 7/2000 |
| DE | 19907646 | A1 | 8/2000 |
| DE | 10049812 | A1 | 4/2002 |
| DE | 10049813 | C1 | 4/2002 |
| DE | 10049814 | A1 | 4/2002 |
| DE | 10049815 | A1 | 4/2002 |
| EP | 0103546 | B1 | 5/1988 |
| EP | 0850607 | A1 | 7/1998 |
| EP | 1057460 | A1 | 12/2000 |
| EP | 1088529 | A2 | 4/2001 |
| EP | 1570809 | A1 | 9/2005 |
| FR | 2788217 | A1 | 7/2000 |
| FR | 2815844 | A1 | 5/2002 |
| GB | 2056023 | A | 3/1981 |
| SU | 1271508 | A1 | 11/1986 |
| WO | 1991017720 | A1 | 11/1991 |
| WO | 1992017118 | A1 | 10/1992 |
| WO | 1993001768 | A1 | 2/1993 |
| WO | 1997024080 | A1 | 7/1997 |
| WO | 1998029057 | A1 | 7/1998 |
| WO | 1999030646 | A1 | 6/1999 |
| WO | 1999033414 | A1 | 7/1999 |
| WO | 1999040964 | A1 | 8/1999 |
| WO | 1999047075 | A1 | 9/1999 |
| WO | 2000018333 | A1 | 4/2000 |
| WO | 2000041652 | A1 | 7/2000 |
| WO | 2000047139 | A1 | 8/2000 |
| WO | 2001035878 | A2 | 5/2001 |
| WO | 2001049213 | A2 | 7/2001 |
| WO | 2001054624 | A1 | 8/2001 |
| WO | 2001054625 | A1 | 8/2001 |
| WO | 2001062189 | A1 | 8/2001 |
| WO | 2001064137 | A1 | 9/2001 |
| WO | 2001076510 | A2 | 10/2001 |
| WO | 2002022054 | A1 | 3/2002 |
| WO | 2002036048 | A1 | 5/2002 |
| WO | 2002041789 | A2 | 5/2002 |
| WO | 2002043620 | A1 | 6/2002 |
| WO | 2002047575 | A2 | 6/2002 |
| WO | 2002049540 | A2 | 6/2002 |
| WO | 2003047468 | A1 | 6/2003 |
| WO | 2005034812 | A1 | 4/2005 |
| WO | 2005055883 | A1 | 6/2005 |
| WO | 2005084595 | A1 | 9/2005 |
| WO | 2005102015 | A2 | 11/2005 |
| WO | 2006014233 | A2 | 2/2006 |
| WO | 2006032051 | A2 | 3/2006 |
| WO | 2006034008 | A2 | 3/2006 |
| WO | 2006111391 | A1 | 10/2006 |
| WO | 2006127089 | A1 | 11/2006 |
| WO | 2006138173 | A2 | 12/2006 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008147964 | A1 | 12/2008 |
| WO | 2008150529 | A1 | 12/2008 |
| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009094188 | A2 | 7/2009 |
| WO | 2009116041 | A2 | 9/2009 |
| WO | 2009149462 | A2 | 12/2009 |
| WO | 2010011699 | A2 | 1/2010 |
| WO | 2010121076 | A2 | 10/2010 |
| WO | 2013106585 | A1 | 7/2013 |
| WO | 2015085218 | A1 | 6/2015 |
| WO | WO-2019067219 | A1 | 4/2019 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al., "Prototype Stent: Invivo Swine Studies in the Biliary System", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

PROSTHETIC HEART VALVE HAVING NON-LINEAR STRUTS

CROSS REFERENCE TO RELATED APPLICATIONS

This application is a continuation of a PCT Patent Application No. PCT/US2020/063205, entitled "PROSTHETIC HEART VALVE HAVING NON-LINEAR STRUTS," filed Dec. 4, 2020, which claims the benefit of U.S. Provisional Application 63/094,459 entitled "PROSTHETIC HEART VALVE HAVING NON-LINEAR STRUTS," filed on Oct. 21, 2020 and U.S. Provisional Application 62/945,000, entitled "PROSTHETIC HEART VALVE HAVING NON-LINEAR STRUTS," filed Dec. 6, 2019, all of which are incorporated by reference herein in their entirety.

FIELD

The present disclosure relates to implantable, mechanically expandable prosthetic devices, such as prosthetic heart valves, and to methods and delivery assemblies for, and including, such prosthetic devices.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery apparatus and advanced through the patient's vasculature (e.g., through a femoral artery and the aorta) until the prosthetic heart valve reaches the implantation site in the heart. The prosthetic heart valve is then expanded to its functional size, for example, by inflating a balloon on which the prosthetic valve is mounted, actuating a mechanical actuator that applies an expansion force to the prosthetic heart valve, or by deploying the prosthetic heart valve from a sheath of the delivery apparatus so that the prosthetic heart valve can self-expand to its functional size.

Prosthetic heart valves that rely on a mechanical actuator for expansion can be referred to as "mechanically expandable" prosthetic heart valves. Mechanically expandable prosthetic heart valves can provide one or more advantages over self-expandable and balloon-expandable prosthetic heart valves. For example, mechanically expandable prosthetic heart valves can be expanded to various diameters. Mechanically expandable prosthetic heart valves can also be compressed after an initial expansion (e.g., for repositioning and/or retrieval). During expansion and compression of the prosthetic valve, and during typical use of the prosthetic valve, various forces can act upon the frame which can deform or bend the frame.

Accordingly, a need exists for improved prosthetic heart valve frame designs and methods for implantation.

SUMMARY

Described herein are embodiments of improved implantable medical devices, such as prosthetic heart valves, as well as methods for implanting such devices.

In a representative embodiment, an implantable prosthetic device can comprise a frame that is radially expandable and compressible between a radially compressed configuration and a radially expanded configuration. The frame can comprise a plurality of struts, each strut comprising a first portion and a second portion separated by a deflection point. Each strut can be curved helically with respect to a first, longitudinal axis of the frame. The first portion of each strut can be curved in a first direction with respect to a first line parallel to a second axis that is perpendicular to the first, longitudinal axis of the frame, and the second portion of each strut can be curved in a second direction with respect to a second line parallel to the second axis.

In another representative embodiment, an implantable prosthetic device comprises a frame having first and second opposing axial ends, the frame comprising a plurality of inner and outer struts pivotably coupled to one another at a plurality of junctions. Each strut has a first portion and a second portion, the first portion forming a convex curve facing the first end of the frame and the second portion forming a concave curve facing the first end of the frame.

In a representative embodiment, an implantable prosthetic device comprises a radially expandable and compressible frame having an inflow end portion and an outflow end portion. The frame can comprise a plurality of first struts extending in a first direction and a plurality of second struts extending in a second direction. The second struts can be coupled to the first plurality of struts at a plurality of junctions, a first set of selected junctions being configured as fastening junctions, and a second set of selected junctions being configured as pivotable junctions. Each fastening junction can comprise a fastener configured to couple a respective first strut and second strut to one another such that the respective first and second struts can pivot relative to one another about the fastener, and each pivotable junction can comprise a protrusion extending from a surface of a respective second strut, the protrusion disposed within a corresponding recess in a surface of a respective first strut such that the respective first and second struts can pivot relative to one another about the protrusion.

In another representative embodiment, an implantable prosthetic device can comprise a radially expandable and compressible frame having an inflow end portion and an outflow end portion. The frame can comprise a plurality of first struts extending in a first direction and a plurality of second struts extending in a second direction and coupled to the plurality of first struts at a plurality of junctions. Each first strut can comprise a plurality of linear segments coupled to one or more adjacent linear segments via one or more intermediate segments, and each first strut can comprise at least one aperture extending through a thickness of the first strut at an intermediate segment and at least one recess extending into the thickness of the first strut at an additional intermediate segment. Each second strut can comprise a plurality of linear segments coupled to one or more adjacent linear segments via one or more intermediate segments, each second strut can further comprise at least one fastener extending from a surface of the strut at an intermediate segment and at least one protrusion extending from the surface of the strut at an additional intermediate segment. Selected junctions of the plurality of junctions can be configured as fastening junctions and selected junctions can be configured as pivotable junctions.

In another representative embodiment, an implantable prosthetic device can comprise a radially expandable and compressible frame having an inflow end portion and an outflow end portion. The frame can comprise a plurality of first struts extending in a first direction, each first strut comprising at least one first aperture extending through a thickness of the first strut and a first recess disposed around the first aperture, and a plurality of second struts extending in a second direction, each second strut comprising at least one second aperture extending through a thickness of the second strut and a second recess disposed around the second aperture. The frame can further comprise a plurality of fasteners, each fastener extending through a respective first aperture and a respective second aperture to couple respective first and second struts to one another at a junction, each fastener comprising a body portion, a head portion sized to retain the fastener within the second recess and a flanged end portion sized to retain the fastener within the first recess.

In a representative embodiment, a method can comprise inserting a fastener through a first aperture in a first strut and a second aperture in a second strut, the fastener comprising a body portion having a first diameter, a head portion having a second diameter larger than the first diameter, and an end portion, and disposing the head portion of the fastener in a recess surrounding the second aperture, the recess disposed in a radially inner surface of the second strut. The method can further comprise deforming the end portion of the fastener to form a flanged head portion disposed in an additional recess surrounding the first aperture to couple the first and second struts to one another such that the first and second struts can pivot relative to one another about the fastener.

In another representative embodiment, an implantable prosthetic device can comprise a radially expandable and compressible frame having an inflow end portion and an outflow end portion. The frame can comprise a plurality of first struts extending in a first direction, each first strut comprising at least one aperture extending through a thickness of the first strut and a recess disposed around the aperture, and a plurality of second struts extending in a second direction, each second strut comprising at least one fastener extending from a surface of the second strut. Each fastener can extend through a respective aperture to couple respective first and second struts to one another at a junction, each fastener comprising a body portion and a flanged end portion sized to retain the fastener within the recess.

In a representative embodiment, a method comprises inserting a fastener through an aperture in a first strut, the fastener extending from a radially outer surface of a second strut, and deforming an end portion of the fastener to form a flanged head portion disposed in a recess surrounding the aperture to couple the first and second struts to one another such that the first and second struts can pivot relative to one another about the fastener, the recess disposed in a radially outer surface of the first strut.

In a representative embodiment, an implantable prosthetic device can comprise a radially expandable and compressible frame having an inflow end portion and an outflow end portion. The frame can comprise a plurality of first struts extending in a first direction, each first strut comprising at least one aperture extending through a thickness of the first strut and a recess disposed around the aperture, and a plurality of second struts extending in a second direction, each second strut comprising at least one fastener extending from a surface of the second strut through a respective aperture in a first strut. Each fastener can comprise a body portion, a protrusion, and an inner slot extending at least partially along a length of the fastener, the fastener being movable between a compressed configuration and an uncompressed configuration. When in the uncompressed configuration the protrusion is sized to retain the fastener within the respective aperture to couple the first and second struts to one another and allow the first and second struts to pivot relative to one another about the fastener.

In a representative embodiment, a method can comprise forcing a fastener against an aperture in a first strut, the fastener extending from a radially outer surface of a second strut and comprising a body portion, a protrusion, and an inner slot extending at least partially along a length of the fastener, the protrusion having a diameter larger than a diameter of the aperture, and advancing the fastener through the aperture such that the fastener moves from an uncompressed configuration to a compressed configuration. The method can further comprise, once the protrusion has emerged from a radially outer end of the aperture, allowing the fastener to resiliently expand to the uncompressed configuration such that the fastener is retained within the aperture to couple the first and second struts to one another such that the first and second struts can pivot relative to one another about the fastener.

The foregoing and other objects, features, and advantages of the disclosure will become more apparent from the following detailed description, which proceeds with reference to the accompanying figures.

DETAILED DESCRIPTION

General Considerations

Figure 1:
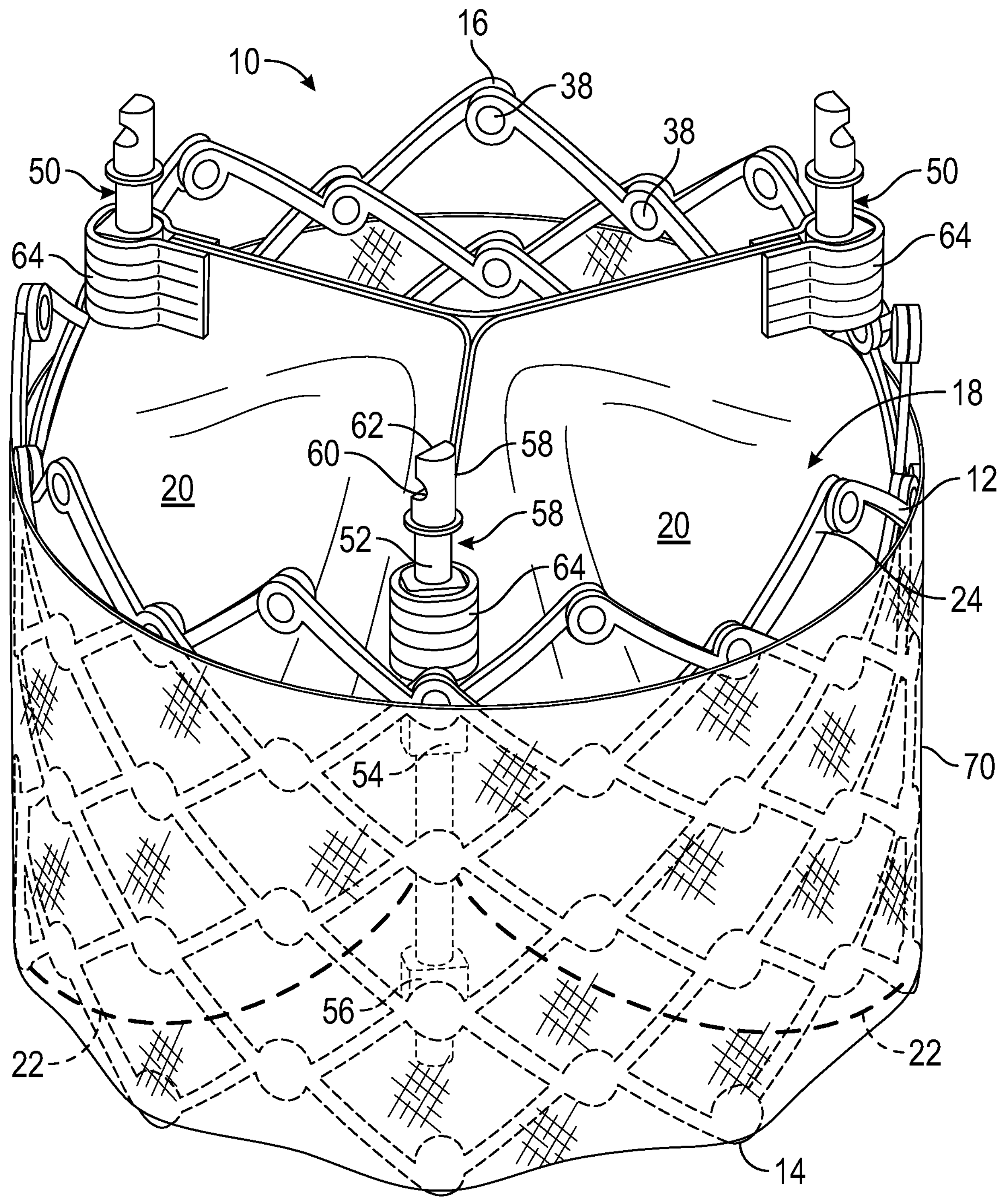
FIG. 1 is a perspective view of a prosthetic heart valve, according to one embodiment.

It should be understood that the disclosed embodiments can be adapted for delivering and implanting prosthetic devices in any of the native annuluses of the heart (e.g., the aortic, pulmonary, mitral, and tricuspid annuluses), and can be used with any of various delivery devices for delivering the prosthetic valve using any of various delivery approaches (e.g., retrograde, antegrade, transseptal, transventricular, transatrial, etc.).

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth herein. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or", as well as "and" and "or."

Examples of the Disclosed Technology

Described herein are embodiments of prosthetic implants, including frames for use in prosthetic implants such as prosthetic heart valves or venous valves, stents, or grafts, to name a few. Disclosed frame shapes can prevent or mitigate buckling or other deformation of the prosthetic valve under stress.

Prosthetic valves disclosed herein can be radially compressible and expandable between a radially compressed state and a radially expanded state. Thus, the prosthetic valves can be crimped on or retained by an implant delivery apparatus in the radially compressed state during delivery, and then expanded to the radially expanded state once the prosthetic valve reaches the implantation site. It is understood that the valves disclosed herein may be used with a variety of implant delivery apparatuses, and examples thereof will be discussed in more detail later.

FIG. 1 shows an exemplary prosthetic valve 10, according to one embodiment. The prosthetic valve 10 can include an annular stent or frame 12 having an inflow end 14 and an outflow end 16. The prosthetic valve 10 can also include a valvular structure 18 which is coupled to and supported inside of the frame 12. The valvular structure 18 is configured to regulate the flow of blood through the prosthetic valve 10 from the inflow end 14 to the outflow end 16.

The valvular structure 18 can include, for example, a leaflet assembly comprising one or more leaflets 20 made of a flexible material. The leaflets 20 can be made from in whole or part, biological material, bio-compatible synthetic materials, or other such materials. Suitable biological material can include, for example, bovine pericardium (or pericardium from other sources). The leaflets 20 can be secured to one another at their adjacent sides to form commissures, each of which can be secured to a respective actuator 50 or the frame 102.

In the depicted embodiment, the valvular structure 18 comprises three leaflets 20, which can be arranged to collapse in a tricuspid arrangement. Each leaflet 20 can have an inflow edge portion 22. As shown in FIG. 1, the inflow edge portions 22 of the leaflets 20 can define an undulating, curved scallop shape that follows or tracks a plurality of interconnected strut segments of the frame 12 in a circumferential direction when the frame 12 is in the radially expanded configuration. The inflow edges of the leaflets can be referred to as a "scallop line."

In some embodiments, the inflow edge portions 22 of the leaflets 20 can be sutured to adjacent struts of the frame generally along the scallop line. In other embodiments, the inflow edge portions 22 of the leaflets 20 can be sutured to an inner skirt, which in turn in sutured to adjacent struts of the frame. By forming the leaflets 20 with this scallop geometry, stresses on the leaflets 20 are reduced, which in turn improves durability of the valve 10. Moreover, by virtue of the scallop shape, folds and ripples at the belly of each leaflet 20 (the central region of each leaflet), which can cause early calcification in those areas, can be eliminated or at least minimized. The scallop geometry also reduces the amount of tissue material used to form valvular structure 18, thereby allowing a smaller, more even crimped profile at the inflow end 14 of the valve 10.

Further details regarding transcatheter prosthetic heart valves, including the manner in which the valvular structure can be mounted to the frame of the prosthetic valve can be found, for example, in U.S. Pat. Nos. 6,730,118, 7,393,360, 7,510,575, 7,993,394, and 8,252,202, U.S. Publication No. 2018/0325665 and U.S. application Ser. No. 16/941,776, all of which are incorporated by reference herein in their entireties.

Figure 2B:
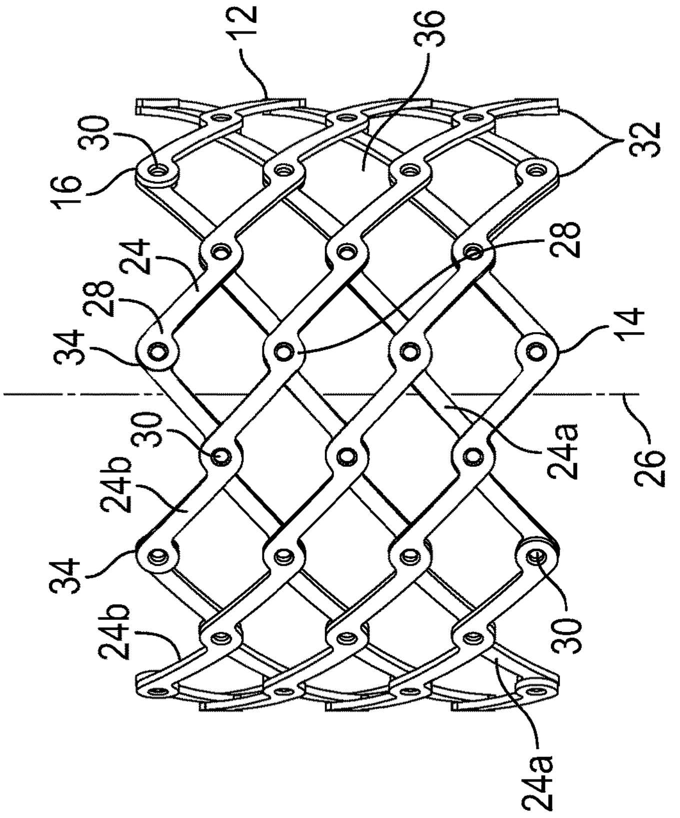
FIG. 2B is a side elevation view of the frame of the prosthetic heart valve of FIG. 1, shown in a radially expanded state.
Figure 2A:
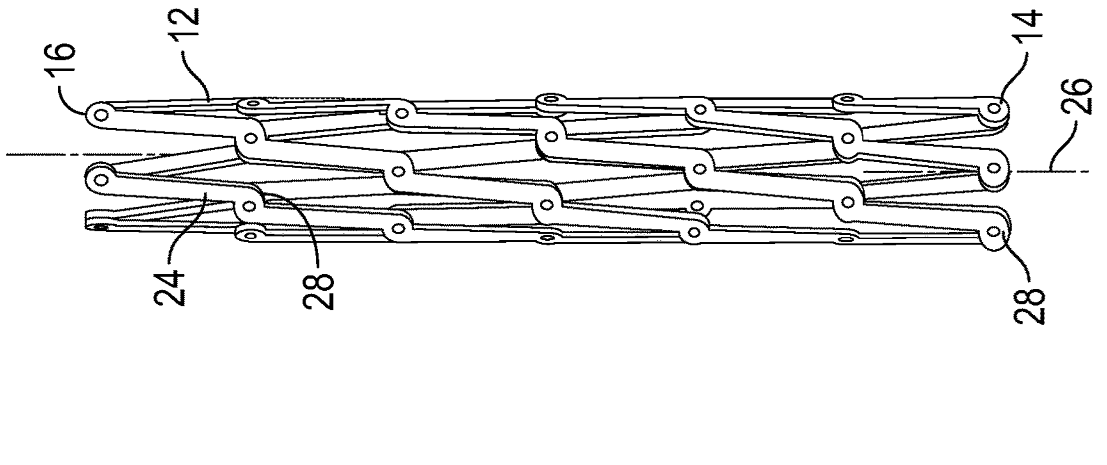
FIG. 2A is a side elevation view of the frame of the prosthetic heart valve of FIG. 1, shown in a radially compressed state.

The prosthetic valve 10 can be radially compressible and expandable between a radially compressed configuration and a radially expanded configuration. FIGS. 2A-2B show the bare frame 12 of the prosthetic valve 10 (without the leaflets and other components) for purposes of illustrating expansion of the prosthetic valve 10 from the radially compressed configuration (FIG. 2A) to the radially expanded configuration (FIG. 2B).

The frame 12 can include a plurality of interconnected lattice struts 24 arranged in a lattice-type pattern and forming a plurality of apices 34 at the outflow end 16 of the prosthetic valve 10. The struts 24 can also form similar apices 32 at the inflow end 14 of the prosthetic valve 10. In FIG. 2B, the struts 24 are shown as positioned diagonally, or offset at an angle relative to, and radially offset from, a longitudinal axis 26 of the prosthetic valve 10 when the prosthetic valve 10 is in the expanded configuration. In other implementations, the struts 24 can be offset by a different amount than depicted in FIG. 2B, or some or all of the struts 24 can be positioned parallel to the longitudinal axis 26 of the prosthetic valve 10.

The struts 24 can comprise a set of inner struts **24*a* (extending from the lower left to the upper right of the frame in FIG. 2B) and a set of outer struts 24*b* (extending from the upper left to the lower right of the frame in FIG. 2B) connected to the inner struts 24*a*. The open lattice structure of the frame 12 can define a plurality of open frame cells 36 between the struts 24**.

The struts 24 can be pivotably coupled to one another at one or more pivot joints or pivot junctions 28 along the length of each strut. For example, in one embodiment, each of the struts 24 can be formed with apertures 30 at opposing ends of the strut and apertures spaced along the length of the strut. Respective hinges can be formed at the locations where struts 24 overlap each other via fasteners 38 (FIG. 1), such as rivets or pins that extend through the apertures 30. The hinges can allow the struts 24 to pivot relative to one another as the frame 12 is radially expanded or compressed, such as during assembly, preparation, or implantation of the prosthetic valve 10.

The frame struts and the components used to form the pivot joints of the frame 12 (or any frames described below) can be made of any of various suitable materials, such as stainless steel, a cobalt chromium alloy, or a nickel titanium alloy ("NiTi"), for example Nitinol. In some embodiments, the frame 12 can be constructed by forming individual components (e.g., the struts and fasteners of the frame) and then mechanically assembling and connecting the individual components together. Further details regarding the construction of the frame and the prosthetic valve are described in U.S. Pat. No. 10,603,165, U.S. Publication Nos. 2018/0344456, 2019/0060057, and 2020/0188099, all of which are incorporated by reference herein.

In the illustrated embodiment, the prosthetic valve 10 can be mechanically expanded from the radially contracted configuration to the radially expanded configuration. For example, the prosthetic valve 10 can be radially expanded by maintaining the inflow end 14 of the frame 12 at a fixed position while applying a force in the axial direction against the outflow end 16 toward the inflow end 14. Alternatively, the prosthetic valve 10 can be expanded by applying an axial force against the inflow end 14 while maintaining the outflow end 16 at a fixed position, or by applying opposing axial forces to the inflow and outflow ends 14, 16, respectively.

As shown in FIG. 1, the prosthetic valve 10 can include one or more actuators 50 mounted to and equally spaced around the inner surface of the frame 12. Each of the actuators 50 can be configured to form a releasable connection with one or more respective actuators of a delivery apparatus.

In the illustrated embodiment, expansion and compression forces can be applied to the frame by the actuators 50. Referring again to FIG. 1, each of the actuators 50 can comprise a screw or threaded rod 52, a first anchor in the form of a cylinder or sleeve 54, and a second anchor in the form of a threaded nut 56. The rod 52 extends through the sleeve 54 and the nut 56. The sleeve 54 can be secured to the frame 12, such as with a fastener 38 that forms a hinge at the junction between two struts. Each actuator 50 is configured to increase the distance between the attachment locations of a respective sleeve 54 and nut 56, which causes the frame 12 to elongate axially and compress radially, and to decrease the distance between the attachment locations of a respective sleeve 54 and nut 56, which causes the frame 12 to foreshorten axially and expand radially.

For example, each rod 52 can have external threads that engage internal threads of the nut 56 such that rotation of the rod causes corresponding axial movement of the nut 56 toward or away from the sleeve 54 (depending on the direction of rotation of the rod 52). This causes the hinges supporting the sleeve 54 and the nut 56 to move closer towards each other to radially expand the frame or to move farther away from each other to radially compress the frame, depending on the direction of rotation of the rod 52.

In other embodiments, the actuators 50 can be reciprocating type actuators configured to apply axial directed forces to the frame to produce radial expansion and compression of the frame. For example, the rod 52 of each actuator can be fixed axially relative to the sleeve 54 and slidable relative to the sleeve 54. Thus, in this manner, moving the rod 52 distally relative to the sleeve 54 and/or moving the sleeve 54 proximally relative to the rod 52 radially compresses the frame. Conversely, moving the rod 52 proximally relative to the sleeve 54 and/or moving the sleeve 54 distally relative to the rod 52 radially expands the frame.

When reciprocating type actuators are used, the prosthetic valve can also include one or more locking mechanisms that retain the frame in the expanded state. The locking mechanisms can be separate components that are mounted on the frame apart from the actuators, or they can be a subcomponent of the actuators themselves.

Each rod 52 can include an attachment member 58 along a proximal end portion of the rod 52 configured to form a releasable connection with a corresponding actuator of a delivery apparatus. The actuator(s) of the delivery apparatus can apply forces to the rods for radially compressing or expanding the prosthetic valve 10. The attachment member 58 in the illustrated configuration comprises a notch 60 and a projection 62 that can engage a corresponding projection of an actuator of the delivery apparatus.

In the illustrated embodiments, the prosthetic valve 10 includes three such actuators 50, although a greater or fewer number of actuators could be used in other embodiments. The leaflets 20 can have commissure attachments members 64 that wrap around the sleeves 54 of the actuators 50. Further details of the actuators, locking mechanisms and delivery apparatuses for actuating the actuators can be found in U.S. Pat. No. 10,603,165 and U.S. Patent Publication Nos. 2019/0060057, 2018/0153689, and 2018/0325665, each of which is incorporated by reference herein in its entirety. Any of the actuators and locking mechanisms disclosed in the previously filed applications can be incorporated in any of the prosthetic valves disclosed herein. Further, any of the delivery apparatuses disclosed in the previously filed applications can be used to deliver and implant any of the prosthetic valves discloses herein.

The prosthetic valve 10 can include one or more skirts or sealing members. In some embodiments, the prosthetic valve 10 can include an inner skirt (not shown) mounted on the inner surface of the frame. The inner skirt can function as a sealing member to prevent or decrease perivalvular leakage, to anchor the leaflets to the frame, and/or to protect the leaflets against damage caused by contact with the frame during crimping and during working cycles of the prosthetic valve. As shown in FIG. 1, the prosthetic valve 10 can also include an outer skirt 70 mounted on the outer surface of the frame 12. The outer skirt 70 can function as a sealing member for the prosthetic valve by sealing against the tissue of the native valve annulus and helping to reduce paravalvular leakage past the prosthetic valve. The inner and outer skirts can be formed from any of various suitable biocompatible materials, including any of various synthetic materials, including fabrics (e.g., polyethylene terephthalate fabric) or natural tissue (e.g., pericardial tissue). Further details regarding the use of skirts or sealing members in prosthetic valve can be found, for example, in U.S. patent application Ser. No. 16/941,776, which is incorporated by reference herein in its entirety.

Figure 4:
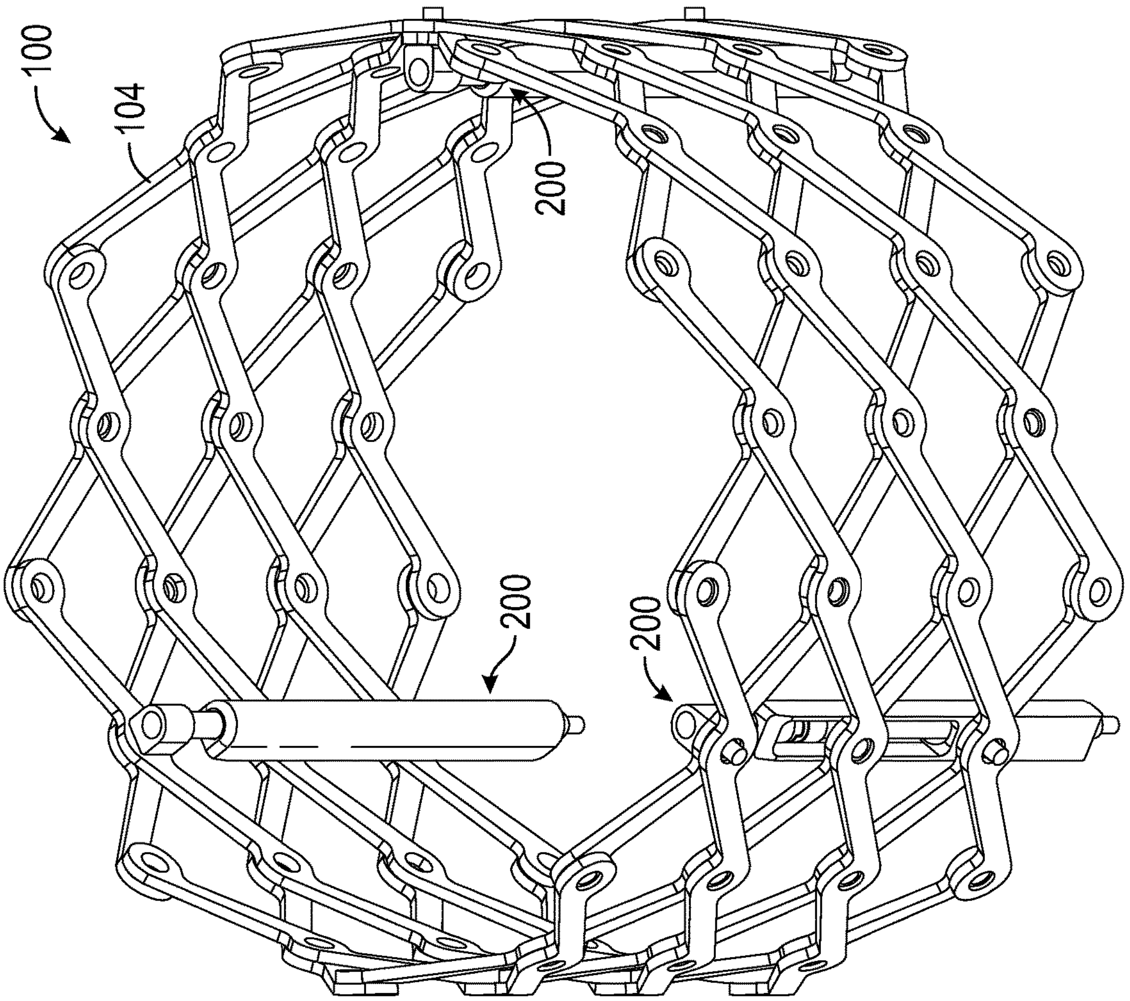
FIG. 4 is a perspective view of the frame and the expansion and locking mechanisms of FIG. 3, with the frame shown in a radially expanded state.
Figure 3:
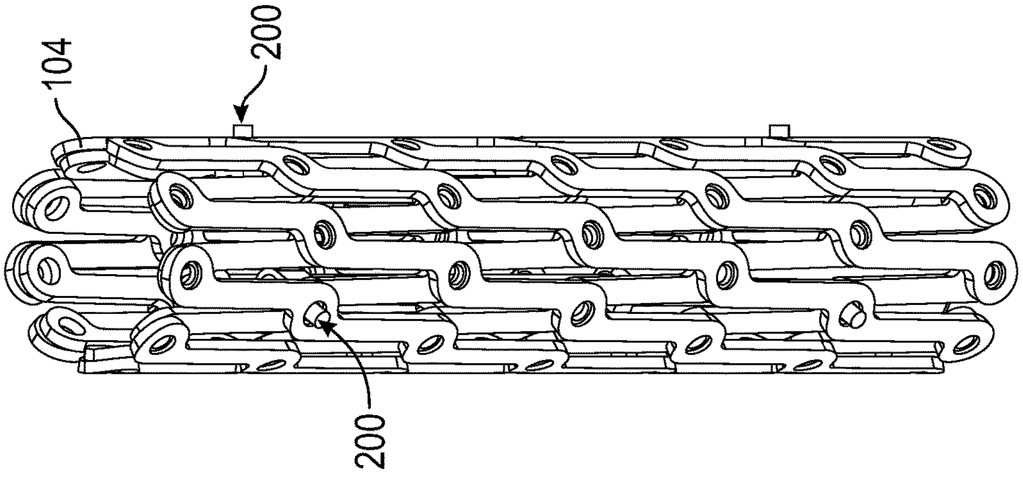
FIG. 3 is a perspective view of a prosthetic valve frame, shown in a radially collapsed state, having a plurality of expansion and locking mechanisms, according to another embodiment.

FIGS. 3-4 show another embodiment of a prosthetic valve 100 comprising a frame 104 and expansion and locking mechanisms 200 (also referred to as "actuators"). It should be understood that the prosthetic valve 100 can include leaflets 20 and other soft components, such as one or more skirts 70, which are removed for purposes of illustration. Expansion and locking mechanism 200 can be used to both radially expand and lock the prosthetic valve in a radially expanded state. In the example of FIGS. 3 and 4, three expansion and locking mechanisms 200 are attached to the frame 104 but in other example delivery assemblies, any number of expansion and locking mechanisms 200 can be used. FIG. 3 shows the expansion and locking mechanisms 200 attached to the frame 104 when the frame is in a radially collapsed configuration and FIG. 4 shows expansion and locking mechanisms attached to the frame when the frame is in a radially expanded configuration.

It will be appreciated that prosthetic valve 100 can, in certain embodiments, use other mechanisms for expansion and locking, such as linear actuators, alternate locking mechanisms, and alternate expansion and locking mechanisms. Further details regarding the use of linear actuators, locking mechanisms, and expansion and locking mechanisms in prosthetic valve can be found, for example, in U.S. Pat. No. 10,603,165, which is incorporated by reference herein in its entirety.

Figure 5C:
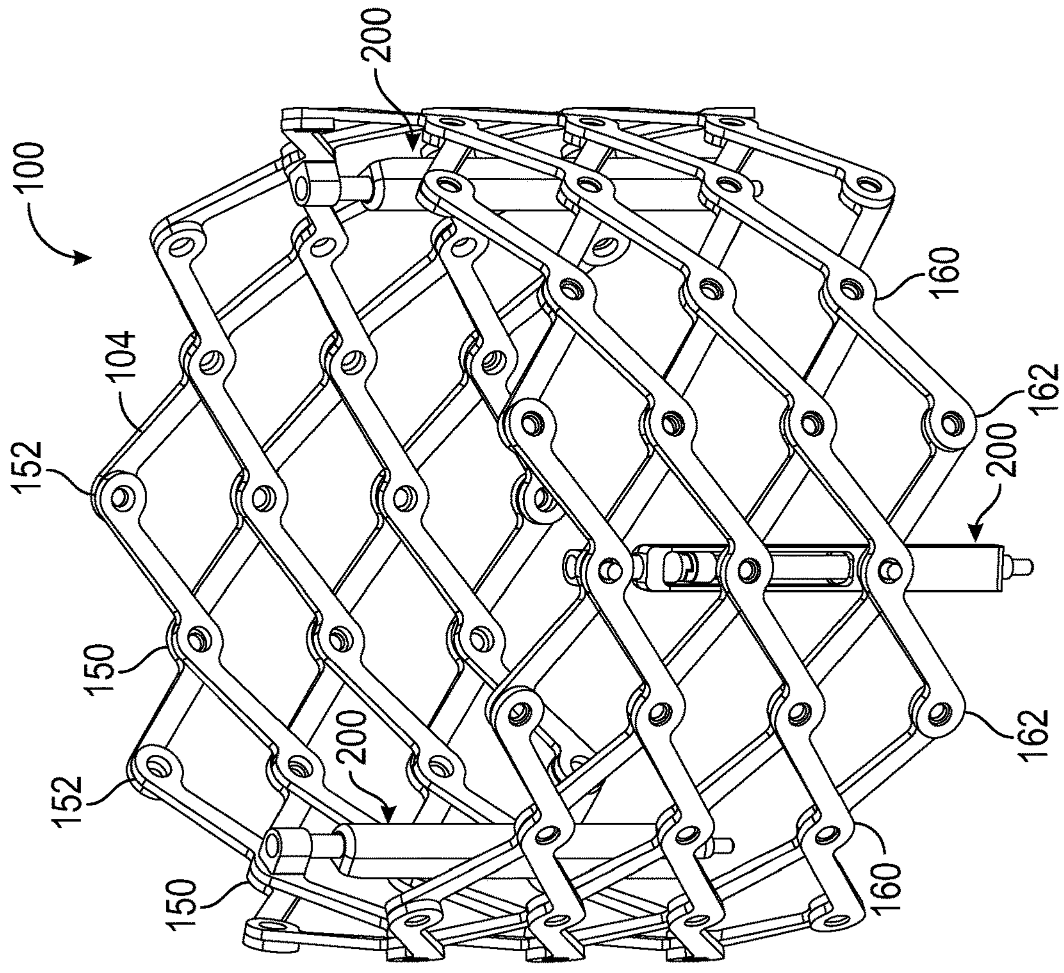
FIG. 5C is another perspective view of the frame and the expansion and locking mechanisms of FIG. 3, with the frame shown in a radially expanded state.
Figure 5B:
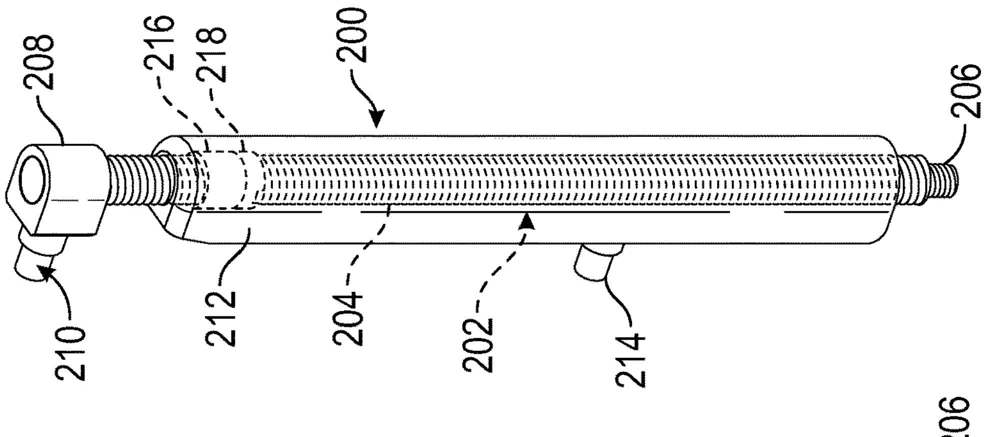
FIG. 5B is a perspective view of one of the expansion and locking mechanisms of FIG. 3.
Figure 5A:
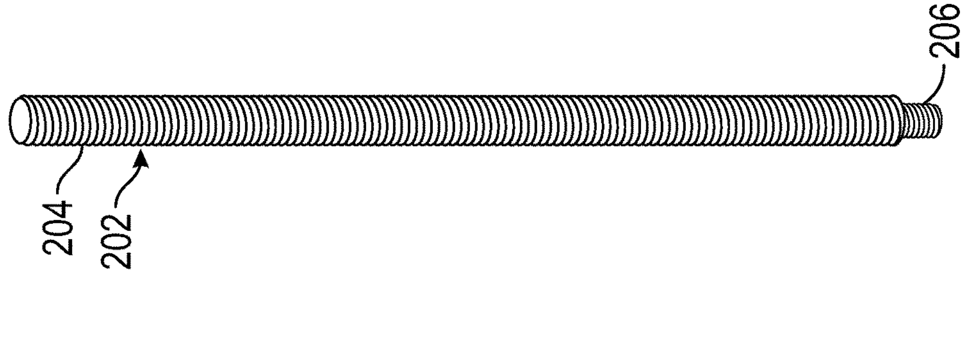
FIG. 5A is a perspective view of a screw of one of the expansion and locking mechanisms of FIG. 3.

Referring to FIGS. 5A-5C, the expansion and locking mechanism 200 in the illustrated embodiment can include an actuator screw 202 (which functions as a linear actuator or a push-pull member in the illustrated embodiment) comprising a relatively long upper, or distal, portion 204 and a relatively shorter lower, or proximal, portion 206 at the proximal end of the screw 200, wherein the lower portion has a smaller diameter than the upper portion. Both the upper and lower portions 204, 206 of the screw 202 can have externally threaded surfaces.

The actuator screw 200 can have a distal attachment piece 208 attached to its distal end having a radially extending distal valve connector 210. The distal attachment piece 208 can be fixed to the screw 202 (e.g., welded together or manufactured as one piece). The distal valve connector 210 can extend through an opening at or near the distal end of the frame 104 formed at a location on the frame where two or more struts intersect as shown in FIG. 5C. The distal valve connector 210 can be fixed to the frame 104 (e.g., welded). Due to the shape of the struts, the distal end of the frame 104 comprises an alternating series of distal junctions 150 and distal apices 152. In the illustrated example, the distal valve connectors 210 of the three expansion and locking mechanisms 200 are connected to the frame 104 through distal junctions 150. In other examples, one or more distal valve connectors 210 can be connected to the frame 104 through distal apices 152. In other embodiments, the distal valve connectors 210 can be connected to junctions closer to the proximal end of the frame 104.

The expansion and locking mechanism 200 can further include a sleeve 212. The sleeve 212 can be positioned annularly around the distal portion 204 of the screw 202 and can contain axial openings at its proximal and distal ends through which the screw 202 can extend. The axial openings and the lumen in the sleeve 212 can have a diameter larger than the diameter of the distal portion 204 of the screw 202 such that the screw can move freely within the sleeve (the screw 202 can be moved proximally and distally relative to the sleeve 212). Because the actuator screw 202 can move freely within the sleeve, it can be used to radially expand and/or contract the frame 104 as disclosed in further detail below.

The sleeve 212 can have a proximal valve connector 214 extending radially from its outer surface. The proximal valve connector 214 can be fixed to the sleeve 212 (e.g., welded). The proximal valve connector 214 can be axially spaced from the distal valve connector 210 such that the proximal valve connector can extend through an opening at or near the proximal end of the frame 104. The proximal end of the frame 104 comprises an alternating series of proximal junctions 160 and proximal apices 162. In the illustrated example, the proximal valve connectors 214 of the three expansion and locking mechanisms 200 are connected to the frame 104 through proximal junctions 160. In other examples, one or more proximal valve connectors 214 can be connected to the frame 104 through proximal apices 162. In other embodiments, the proximal valve connectors 214 can be connected to junctions closer to the distal end of the frame 104.

It should be understood that the distal and proximal connectors 210, 214 need not be connected to opposite ends of the frame. The actuator 200 can be used to expand and compress the frame as long as the distal and proximal connectors are connected to respective junctions on the frame that are axially spaced from each other.

A locking nut 216 can be positioned inside of the sleeve 212 and can have an internally threaded surface that can engage the externally threaded surface of the actuator screw 202. The locking nut 216 can have a notched portion 218 at its proximal end, the purpose of which is described below. The locking nut can be used to lock the frame 104 into a particularly radially expanded state, as discussed below.

Figure 6:
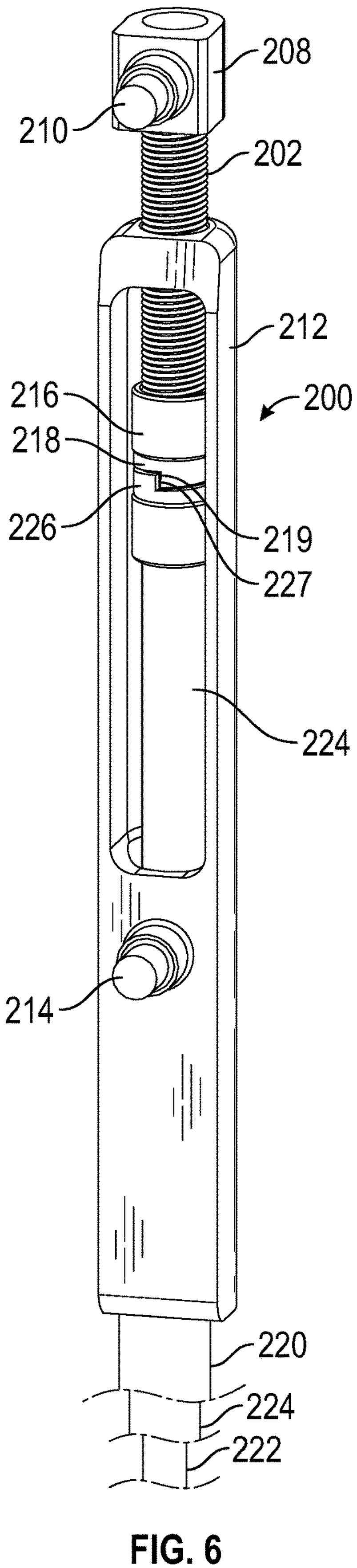
FIG. 6 is another perspective view of one of the expansion and locking mechanisms of FIG. 3.
Figure 7:
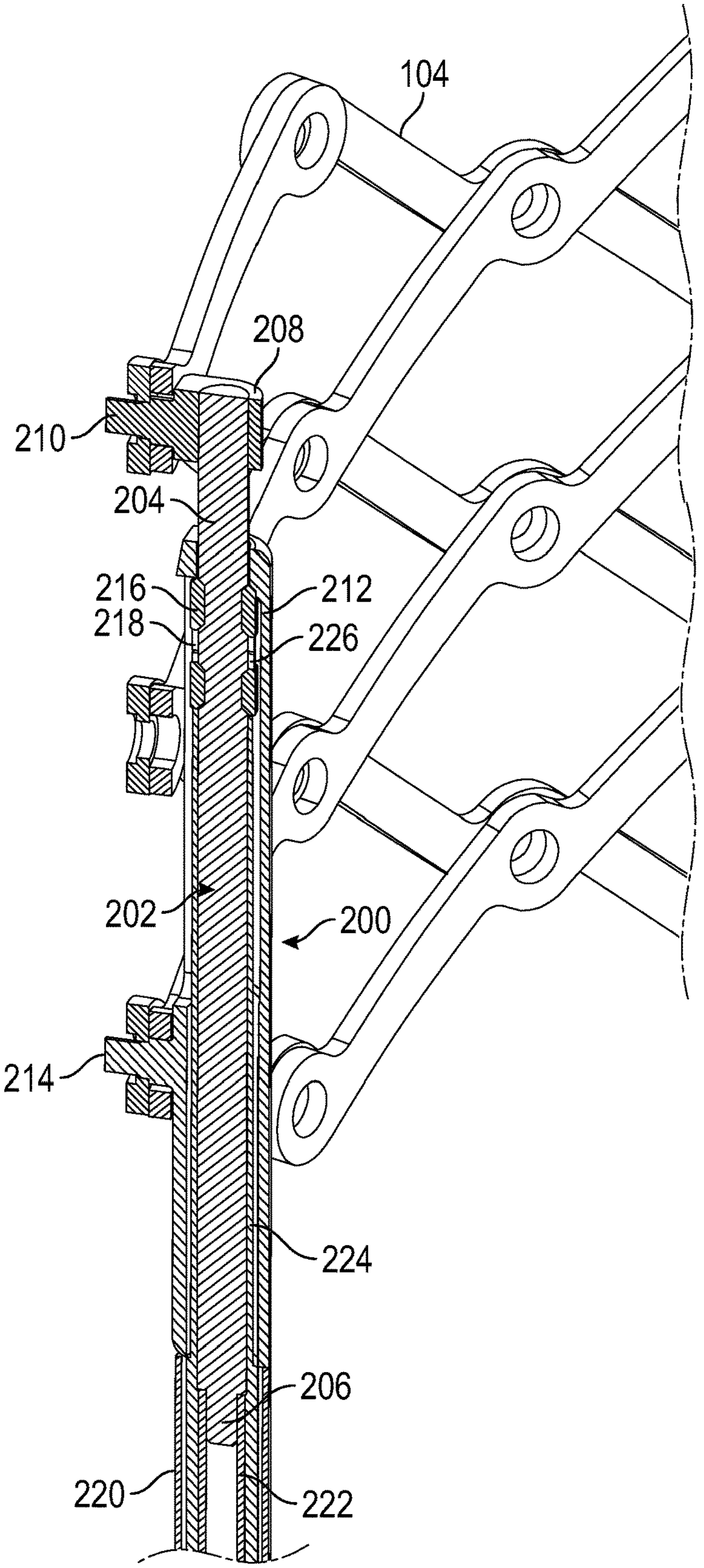
FIG. 7 shows a cross sectional view of one of the expansion and locking mechanisms of FIG. 3 along with a portion of the frame.

FIGS. 6 and 7 shows the expansion and locking mechanism 200 including components of a delivery apparatus not shown in FIGS. 5A-5C. As shown, the expansion and locking mechanism 200 can be releasably coupled to a support tube 220, an actuator member 222, and a locking tool 224. The proximal end of the support tube 220 can be connected to a handle or other control device (not shown) that a doctor or operator of the delivery assembly utilizes to operate the expansion and locking mechanism 200 as described herein. Similarly, the proximal ends of the actuator member 222 and the locking tool 224 can be connected to the handle.

The support tube 220 annularly surrounds a proximal portion of the locking tool 224 such that the locking tool extends through a lumen of the support tube. The support tube 220 and the sleeve are sized such that the distal end of the support tube abuts or engages the proximal end of the sleeve 212 such that the support tube is prevented from moving distally beyond the sleeve.

The actuator member 222 extends through a lumen of the locking tool 224. The actuator member 222 can be, for example, a shaft, a rod, a cable, or wire. The distal end portion of the actuator member 222 can be releasably connected to the proximal end portion 206 of the actuator screw 202. For example, the distal end portion of the actuator member 222 can have an internally threaded surface that can engage the external threads of the proximal end portion 206 of the actuator screw 202. Alternatively, the actuator member 222 can have external threads that engage an internally threaded portion of the screw 202. When the actuator member 222 is threaded onto the actuator screw 202, axial movement of the actuator member causes axial movement of the screw.

The distal portion of the locking tool 224 annularly surrounds the actuator screw 202 and extends through a lumen of the sleeve 212 and the proximal portion of the locking tool annularly surrounds the actuator member 222 and extends through a lumen of the support tube 220 to the handle of the delivery device. The locking tool 224 can have an internally threaded surface that can engage the externally threaded surface of the locking screw 202 such that clockwise or counter-clockwise rotation of the locking tool 224 causes the locking tool to advance distally or proximally along the screw, respectively.

The distal end of the locking tool 224 can comprise a notched portion 226, as can best be seen in FIG. 6. The notched portion 226 of the locking tool 224 can have an engagement surface 227 that is configured to engage a correspondingly shaped engagement surface 219 of the notched portion 218 of the locking nut 216 such that rotation of the locking tool (e.g., clockwise rotation) causes the nut 216 to rotate in the same direction (e.g., clockwise) and advance distally along the locking screw 202. The notched portions 218, 226 in the illustrated embodiment are configured such that rotation of the locking tool 224 in the opposite direction (e.g., counter-clockwise) allows the notched portion 226 of the tool 224 to disengage the notched portion 218 of the locking nut 216; that is, rotation of the locking tool in a direction that causes the locking tool to move proximally does not cause corresponding rotation of the nut.

In alternative embodiments, the distal end portion of the locking tool 224 can have various other configurations adapted to engage the nut 216 and produce rotation of the nut upon rotation of the locking tool for moving the nut distally, such as any of the tool configurations described herein. In some embodiments, the distal end portion of the locking tool 224 can be adapted to produce rotation of the nut 216 in both directions so as move the nut distally and proximally along the locking screw 202.

In operation, prior to implantation, the actuator member 222 is screwed onto the proximal end portion 206 of the actuator screw 202 and the locking nut 216 is rotated such that it is positioned at the proximal end of the screw. The frame 104 can then be placed in a radially collapsed state and the delivery assembly can be inserted into a patient. Once the prosthetic valve is at a desired implantation site, the frame 104 can be radially expanded as described herein.

To radially expand the frame 104, the support tube 220 is held firmly against the sleeve 212. The actuator member 222 is then pulled in a proximal direction through the support tube, such as by pulling on the proximal end of the actuator member or actuating a control knob on the handle that produces proximal movement of the actuator member. Because the support tube 220 is being held against the sleeve 212, which is connected to a proximal end of the frame 104 by the proximal valve connector 214, the proximal end of the frame is prevented from moving relative to the support tube. As such, movement of the actuator member 222 in a proximal direction causes movement of the actuator screw 202 in a proximal direction (because the actuator member is threaded onto the screw), thereby causing the frame 104 to foreshorten axially and expand radially. Alternatively, the frame 104 can be expanded by moving the support tube 220 distally while holding the actuator member 222 stationary or moving the support tube distally while moving the actuator member 222 proximally.

After the frame 104 is expanded to a desired radially expanded size, the frame can be locked at this radially expanded size as described herein. Locking the frame can be achieved by rotating the locking tool 224 in a clockwise direction causing the notched portion 226 of the locking tool to engage the notched portion 218 of the locking nut 216, thereby advancing the locking nut distally along the actuator screw 202. The locking tool 224 can be so rotated until the locking nut 216 abuts an internal shoulder at the distal end of the sleeve 212 and the locking nut 216 cannot advance distally any further (see FIG. 6). This will prevent the screw 202 from advancing distally relative to the sleeve 212 and radially compressing the frame 104. However, in the illustrated embodiment, the nut 216 and the screw 202 can still move proximally through the sleeve 212, thereby allowing additional expansion of the frame 104 either during implantation or later during a valve-in-valve procedure.

Once the frame 104 is locked in radially expanded state, the locking tool 224 can be rotated in a direction to move the locking tool proximally (e.g., in a counter-clockwise direction) to decouple the notched portion 226 from the notched portion 218 of the locking nut 216 and to unscrew the locking tool from the actuator screw 202. Additionally, the actuator member 222 can be rotated in a direction to unscrew the actuator member from the lower portion 206 of the actuator screw 202 (e.g., the actuator member 222 can be configured to disengage from the actuator screw when rotated counter-clockwise). Once the locking tool 224 and the actuator member 222 are unscrewed from the actuator screw 202, they can be removed from the patient along with the support tube 220, leaving the actuator screw and the sleeve 212 connected to the frame 104, as shown in FIG. 5C, with the frame 104 locked in a particular radially-expanded state.

In an alternative embodiment, the locking tool 224 can be formed without internal threads that engage the external threads of the actuator screw 202, which can allow the locking tool 224 to be slid distally and proximally through the sleeve 212 and along the actuator screw 202 to engage and disengage the nut 216.

In some embodiments, additional designs for expansion and locking mechanisms can be used instead of the design previously described. Details on expansion and locking mechanisms can be found, for example, in U.S. Pat. No. 10,603,165, which is incorporated by reference herein in its entirety.

Figure 8:
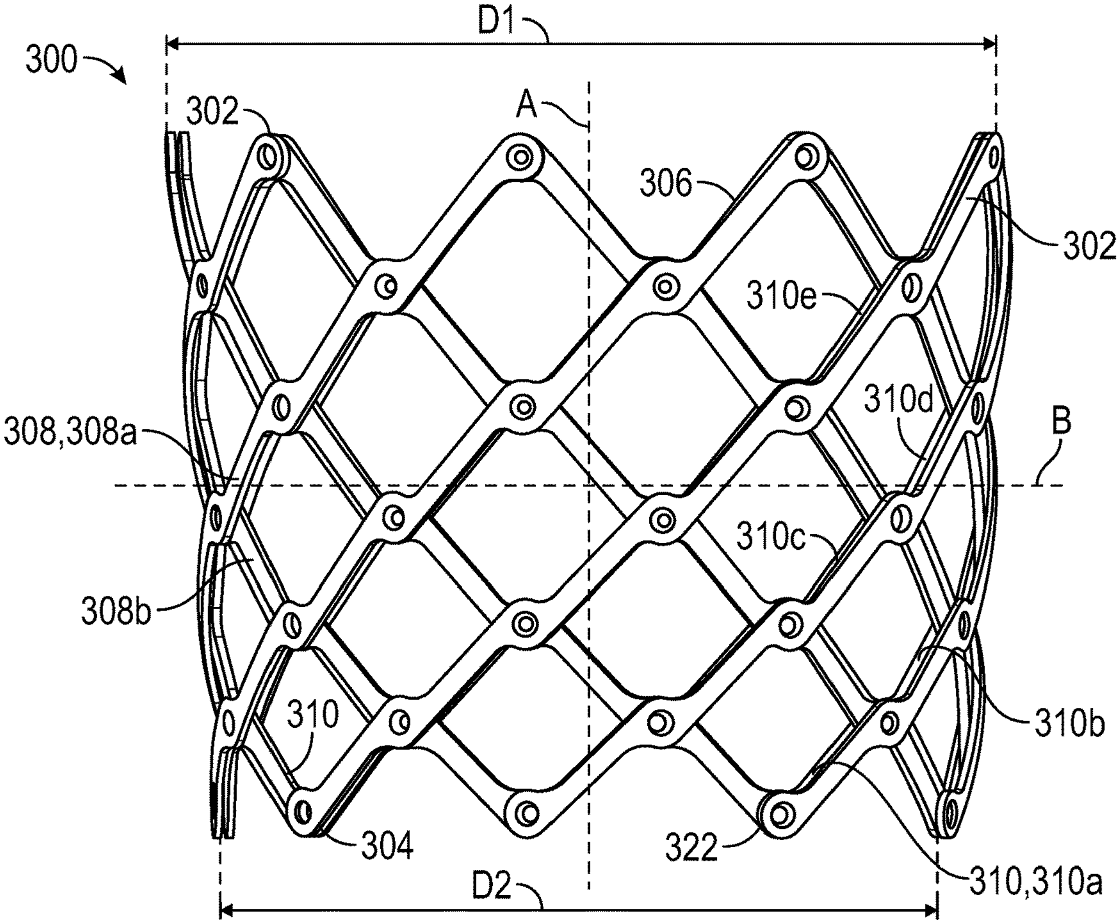
FIG. 8 is a side elevational view of a frame for a prosthetic heart valve, according to another embodiment.

FIG. 8 illustrates another embodiment of a prosthetic valve 300 comprising a frame 302 shown in its deployed, radially expanded configuration. The prosthetic valve 300 can include valvular structure (e.g., valvular structure 18), inner and/or outer skirts, and actuators (e.g., actuators 50) as previously described, although these components are omitted for purposes of illustration. The frame 302 can have an inflow end 304 and an outflow end 306. The prosthetic valve 300 can define a longitudinal axis A extending from the inflow end 304 to the outflow end 306 and a lateral axis B extending perpendicular to the longitudinal axis A. While only one side of the frame 302 is depicted in FIG. 8, it should be appreciated that frame 302 forms an annular structure having an opposite side that is identical to the portion shown.

The frame 302 comprises a plurality of interconnected struts 308 arranged in a lattice-type pattern. Each strut 308 can fully extend from the inflow end 304 of the frame 302 to the outflow end 306. Thus, in the illustrated embodiment, the frame 302 can be formed entirely from struts that extend continuously from the inflow end 304 to the outflow end 306. In alternative embodiments, the frame 302 can have struts that are connected end-to-end along the length of the frame. Each strut can comprise one or more curved portions, as discussed in more detail below.

The struts 308 can comprise a set of radially inner struts (extending from the upper left to the lower right of the frame in FIG. 8) and a set of radially outer struts (extending from the lower left to the upper right of the frame in FIG. 8). The open lattice structure of the frame 302 can define a plurality of frame cells 310 between the struts 308.

As shown in FIG. 8, each strut 308 can be curved helically with respect to the longitudinal axis A of the frame to define an annular shape of the frame 302. The helical curve provides each strut with a concave, radially inner surface (the surface facing longitudinal axis A) and an opposing convex, radially outer surface (the surface facing away from longitudinal axis A).

Figure 9:
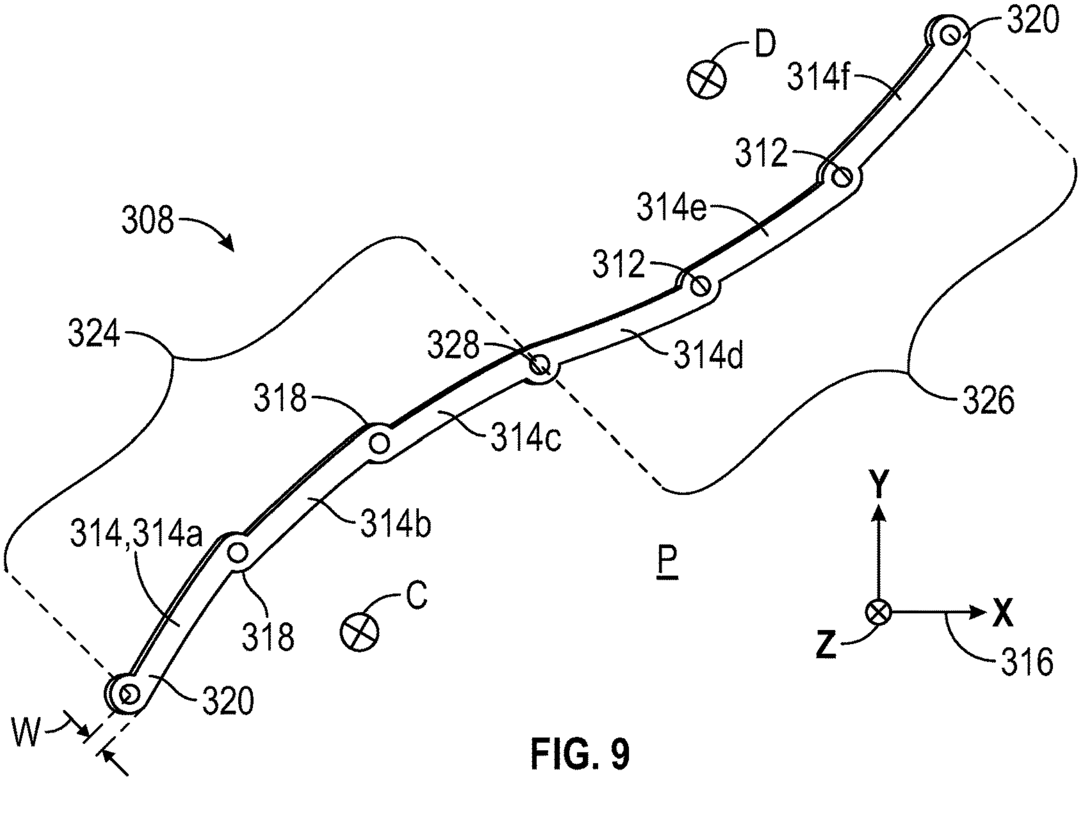
FIG. 9 is a plan view of a strut of the frame of FIG. 8 shown in a flattened configuration.

FIG. 9 shows a flattened projection of a single strut 308 in a plane P parallel to the longitudinal axis A of the frame 302. The plane P is an XY-plane (see e.g., the coordinate system 316) from which axes C and D extend parallel to the Z-axis and perpendicular to the longitudinal axis A and the plane P. FIG. 9 shows the curvature of the strut 308 in an exaggerated fashion for purposes of illustration. However, in other embodiments, the curvature of the strut 308 may be less pronounced than shown.

As shown in FIG. 9, each of the struts 308 can comprise a plurality of apertures 312. The apertures 312 can be spaced along the length of the strut 308. For example, the apertures 312 can be spaced unequally along the length of the strut 308, defining a plurality of segments 314. In the illustrated embodiment, the strut 308 comprises segments **314*a*, 314*b*, 314*c*, 314*d*, 314*e*, 314*f*. Segments 314*a* and 314*b* have a first length, segments 314*c* and 314*d* have a second length greater than the first length, and segments 314*e*, 314*f* have a third length greater than the first and second lengths. In other embodiments, the apertures 312 can be spaced equally along the length of the strut 308 and can define a plurality of equal segments 314**.

In the illustrated embodiment, each segment 314 has an equal width W. However, in other embodiments, the width of each segment 314 can vary along the length of the strut 308. For example, the width of segment **314*a* adjacent the inflow end portion 304 of the frame 302 can be greater than the width of segment 314*f* adjacent the outflow end portion 306** of the frame, or vice versa.

As shown, segments 314 can be arranged end-to-end relative to each other with adjacent ends interconnected to each other by intermediate segments 318. The strut 308 can have enlarged (relative to segments 314) end portions 320 that form apices 322 at the inflow and outflow ends 304, 306 of the frame 302. Each of the intermediate segments 318 and end portions 320 can have a respective aperture 312, such as at its geometric center, for receiving a fastener. Each segment 314 can be slightly laterally offset from an adjacent segment 314 in a direction perpendicular to the overall length of the strut 308, as shown. In alternative embodiments, the segments 314 can be arranged without any offset relative to each other.

The strut 308 can comprise a first, or lower portion 324 and a second, or upper portion 326. The first portion 324 can be positioned adjacent the inflow end 304 and the second portion 326 can be positioned adjacent the outflow end 306. The portions 324, 326 can be separated by a deflection point 328. In the illustrated embodiment, the first portion 324 is curved with respect to a line C parallel to the lateral axis B and positioned between the first portion 324 and the inflow end of the frame 302. This configuration can be considered convex with respect to the outflow end 306 of the frame, and first portion 324 can also be referred to as a "convex portion". The second portion 326 is curved with respect to a line D parallel to the lateral axis B and positioned between the second portion 326 and the outflow end 306 of the frame 302. This configuration can be considered concave with respect to the outflow end 306 of the frame, and second portion 326 can also be referred to as a "concave portion."

In other words, the first portion 324 can be thought of as a straight bar that has been bent around line C (which extends into and out of the plane P) to form a convex curve, and the second portion 326 can be thought of as a straight bar that has been bent around line D (which extends into and out of the plane P) to form a concave curve. This configuration is such that the overall shape of the strut 308 is sinusoidal. As used in the present application, a component, such as a strut or strut segment, being curved with respect to a particular axis means that the component curves around that axis and that axis is parallel to a line that is perpendicular to plane P and extends through the center of curvature of the curve. The curved portions 324, 326 of the struts 308 can provide the frame with additional resistance against buckling or other deformation during expansion or use of the prosthetic valve 300.

In the illustrated embodiment, the deflection point 328 is positioned at a midpoint along the length of the strut such that the first portion 324 and the second portion 326 have equal lengths. In other embodiments, the deflection point 328 can be positioned at any location along the length of the strut 308 such that the first and second portions 324, 326 have unequal lengths. In some particular embodiments, positioning the deflection point 328 such that the convex portion 324 is shorter than the concave portion 326 can improve the resistance of the frame 302 to buckling at the inflow end 304. For example, during expansion of the frame.

In other embodiments, each strut 308 can have two or more deflection points, defining three or more strut portions. For example, a strut can have a first portion configured as a concave portion, a second portion configured as a convex portion, and a third portion configured as a concave portion. In other embodiments, the strut can have any number or portions and the portions configured as concave or convex portions and arranged in any order.

In particular embodiments, each portion 324, 326 can have a continuous and constant curve from one end of the portion to the deflection point 328. For example, each segment 314 of a portion 324, 326 can have a curved shape contributing to the overall curved shape. In other embodiments, each segment 314 can be straight (except for any helical curvature with respect to the longitudinal axis A) and the amount of offset of each segment 314 relative to an adjacent segment 314 along the length of a portion 324, 326 can vary such that the overall shape of each portion 324, 326 is curved along its length with respect to the lateral axis B. Alternatively, individual strut segments 314 can be straight and can be connected end-to-end to each other at non-zero angles such that each portion 324, 326 is curved along its length.

Figure 10:
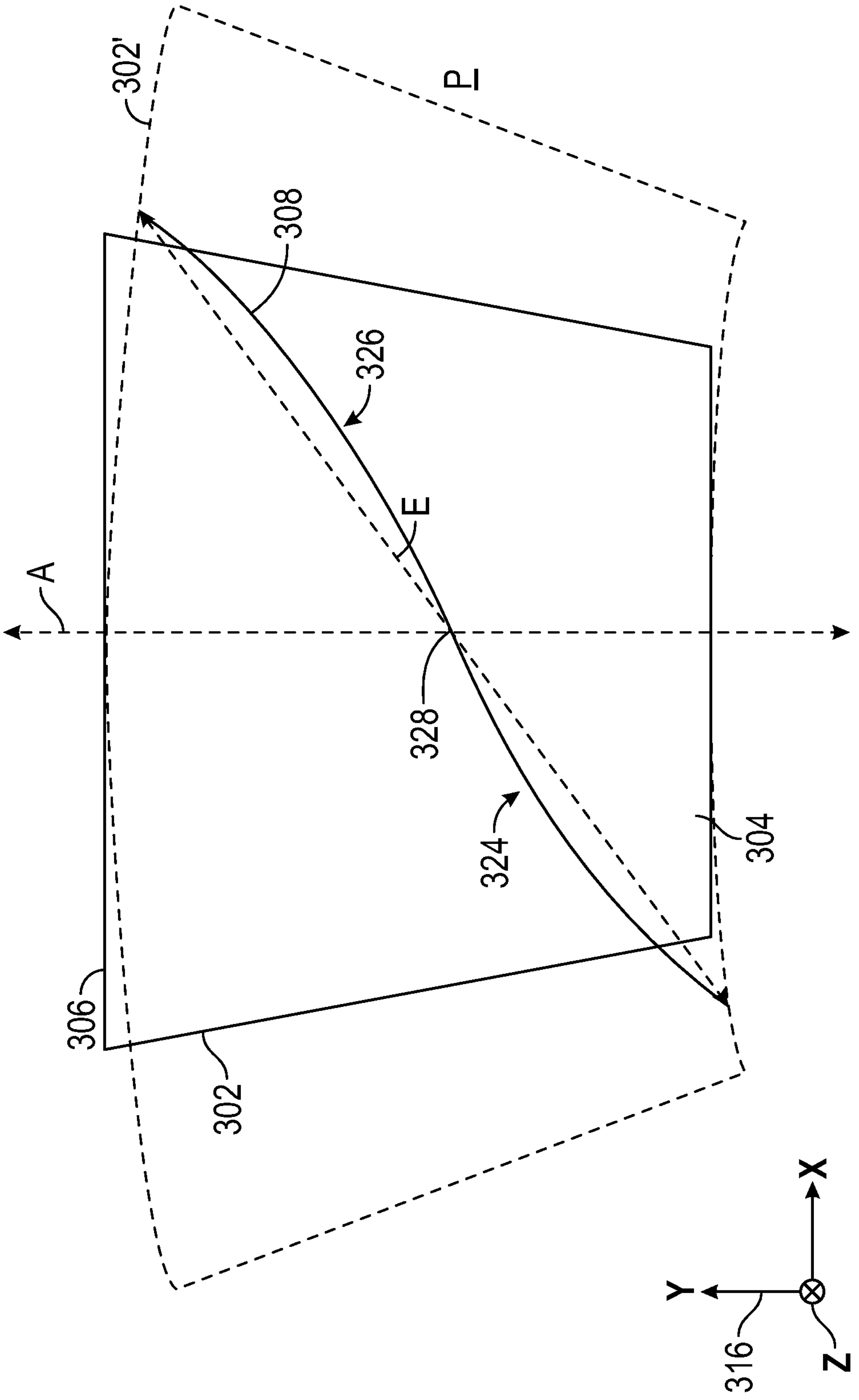
FIG. 10 is a plan view of a strut of the frame of FIG. 8 shown in a flattened configuration.

FIG. 10 shows the outline of frame 302 superimposed over frame 302', which is the frame 302 in an unrolled or unwrapped configuration in a plane P defined by the X- and Y-axes of the shown coordinate system 316. For any strut 308 of the frame 302, a diagonal line or axis E extending through the ends of the strut 308 and the inflow and outflow ends 304, 306 of the frame 302 can be drawn, wherein axis E forms an arbitrary angle with axis A. From left to right, the first portion 324 of each strut 308 curves away from the axis E toward the outflow end, then back toward the axis E at the deflection point 328, and the second portion 326 curves away from axis E toward the inflow end 304, and then back toward axis E at the end of the strut 308.

The degree of curvature of each strut portion 324, 326 in the plane P can be defined as the reciprocal of the radius of a circle comprising the portion of the strut as an arc, as shown in the following equation:

$$K_S = \frac{1}{R}; \qquad \text{Equation 1}$$

where $K_s$=the curvature of the strut portion, and R=the radius of a circle comprising the portion 324, 326 the strut 308 as an arc of the circle.

In the illustrated embodiment, the first and second portion 324, 326 each have approximately the same degree of curvature. However, in other embodiments, each portion 324, 326 can have a differing degree of curvature in the plane P. In still other embodiments, one or more of the portions can be straight in the plane P. For example, a strut can have a first portion configured as a straight portion and a second portion configured as a convex or concave portion. In some embodiments, due to the elasticity of the struts and the connections between overlapping struts, the degree of curvature of portions of a strut can change during radial expansion and compression of the frame. In the radially compressed configuration, each portion 324, 326 can be deformed such that it has a lesser degree of curvature (for example, each portion can be straighter or straight in the plane P) than when in the radially expanded configuration.

Depending on the positioning of the deflection point 328 in each strut 308, in the expanded configuration the assembled frame 302 can have any of various shapes. For example, in some embodiments, such as the illustrated embodiment, the position of the deflection point 328 can give the frame 302 a non-cylindrical, tapered shape wherein the outflow end 306 has a first diameter D1 larger than a second diameter D2 of the inflow end 304. In other embodiments, the position of the deflection point can give the frame 302 a tapered shape where the second diameter D2 is larger than the first diameter D1. In still other embodiments, the deflection point 328 can be positioned to give the frame a cylindrical shape, a frustoconical shape, a V-shape, and/or a Y-shape.

As shown in FIG. 8, in the assembled frame 302, the struts 308 form a plurality of cells 310 arranged in a plurality of circumferentially extending rows of cells having varying sizes. In the illustrated embodiment, each strut 308 has seven apertures 312 (FIG. 9) defining six segments 314 and five rows of cells, including a first row of cells 310*a*, a second row of cells 310*b*, a third row of cells 310*c*, a fourth row of cells 310*d*, and a fifth row of cells 310*e*. In the illustrated embodiment, the rows of cells 310 can have varying sizes. For example, in some embodiments the cells in row 310*a* are the smallest, with subsequent cells 310*b*, 310*c*, 310*d*, and 310*e* being progressively larger. In other embodiments, cells 310*a* and 310*e* can be smaller than cells 310*b*, 310*c*, and 310*d*. However, in still other embodiments, such as the embodiment shown in FIG. 11, cells 310*a* can be smaller than cells 310*b*, which can be smaller than center cells 310*c*, and cells 310*e* can be smaller than cells 310*d*, which can be smaller than the center cells 310*c*. In other embodiments, each strut 308 can have a greater or fewer number of apertures 312 to define a different number of strut segments and rows of frame cells.

The smaller cells, such as cells 310*a* in the illustrated embodiment, can mitigate bending or deformation of the frame 302. For example, in some instances proximally-directed forces applied to the inflow end 304 of the frame 302 during expansion of the prosthetic valve 300 using actuators (e.g., actuators 50) can cause deformation and/or buckling of the frame 302. The smaller cells have a greater structural strength and can therefore prevent or mitigate such deformation. Additionally, the frame 302 can be positioned within the native annulus such that the smaller cells 310*a* bear a greater amount of radial force applied by the native annulus than the larger cells, such as cells 310*c* and 310*d*.

The larger cells, such as cells 310*c* and 310*d* in the illustrated embodiment, can be sized to allow access to the coronary vessel when the prosthetic valve 300 is implanted within the native annulus of a patient. For example, in some instances a patient may require implantation of a coronary stent (or other procedure that requires access to the coronary vessel) after a prosthetic heart valve, such as prosthetic valve 300, has been implanted. In such instances, the physician may access the coronary vessel through the outflow end 306 of the prosthetic valve by passing through the larger cells 310*c*, 310*d* of the frame 302. This allows a physician to access the coronary vessel without needing to remove or displace the prosthetic heart valve.

Figure 11:
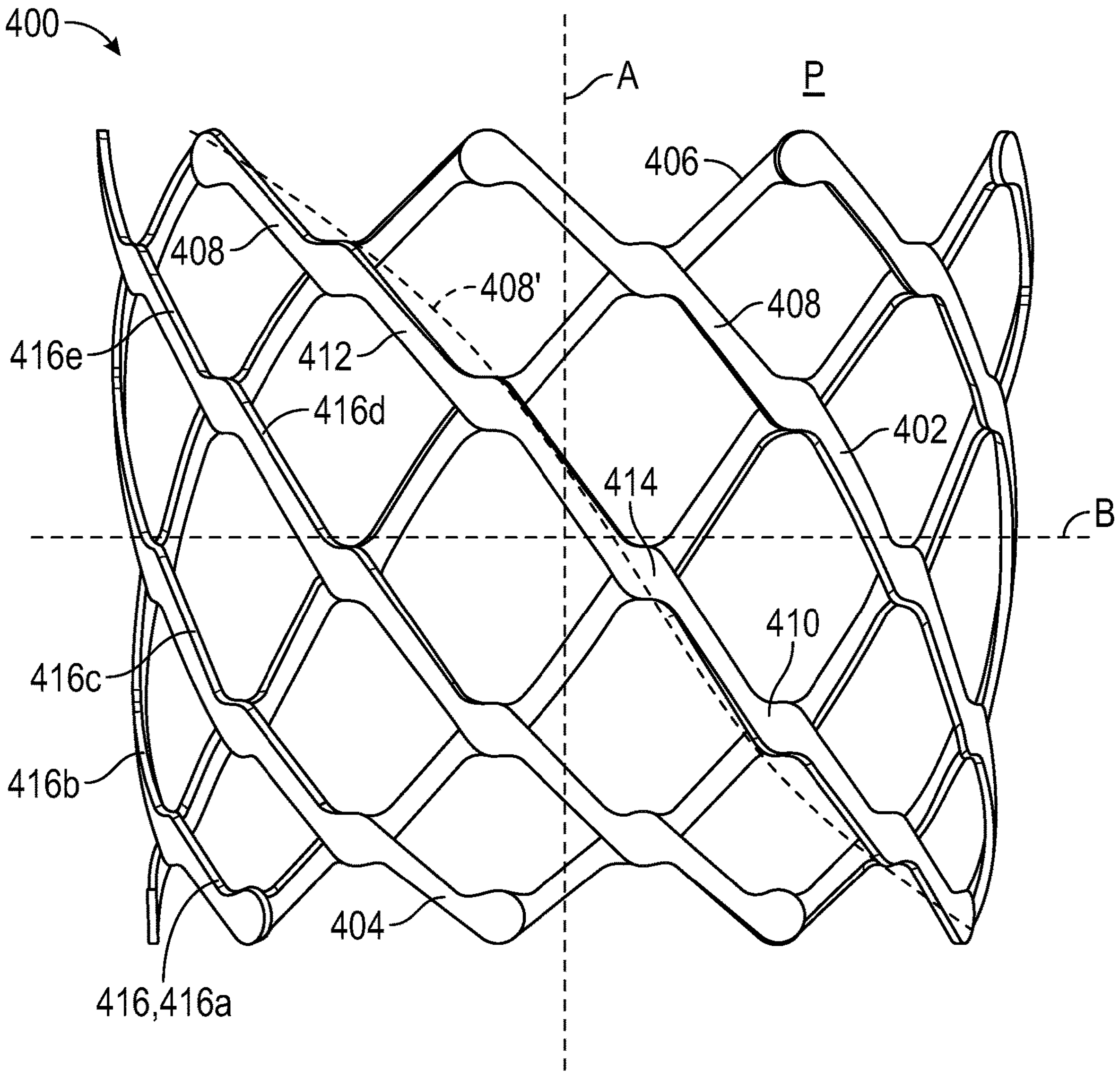
FIG. 11 is a side elevational view of a frame for a prosthetic heart valve, according to another embodiment.

FIG. 11 illustrates an alternative embodiment of a prosthetic heart valve 400. The prosthetic valve 400 is similar to the prosthetic valve 300 except that the prosthetic valve 400 has a frame 402 wherein each strut 408 has a first portion 410 configured as a concave portion and a second portion 412 configured as a convex portion. The prosthetic valve 400 can include a valvular structure (e.g., valvular structure 18), inner and/or outer skirts, and actuators (e.g., actuators 50) as previously described, although these components are omitted for purposes of illustration. Frame 402 has an inflow end 404 and an outflow end 406. While only one side of the frame 402 is depicted in FIG. 11, it should be appreciated that frame 402 forms an annular structure having an opposite side that is identical to the portion shown.

The first, or lower portion 410 of each strut 408 can be positioned adjacent the inflow end 404 of the prosthetic valve 400 and the second, or upper portion 412 of each strut 408 can be positioned adjacent the outflow end 406. The two portions 410, 412 can be separated by a deflection point 414.

As illustrated in an exaggerated fashion by line 408', the first portion 410 can be concave with respect to the outflow end 406 of the frame 402. In other words, the first portion 410 can be thought of as a straight bar that has been bent around a line positioned between the first portion 410 and the outflow end 406 and extending into and out of the plane P to form a concave curve. The second portion 412 can be convex with respect to the outflow end 406. In other words, the second portion 412 can be thought of as a straight bar that has been bent around a line positioned between the second portion 412 and the inflow end 404 and extending into and out of the plane P to form a convex curve. The alternating concave and convex portions give the strut 408 an overall sinusoidal shape.

As shown in FIG. 11, each strut 408 can be curved helically with respect to the longitudinal axis A of the frame to define an annular shape of the frame 402. The helical curve provides each strut with a concave, radially inner surface (the surface facing longitudinal axis A) and an opposing convex, radially outer surface (the surface facing away from longitudinal axis A). As mentioned previously with respect to frame 302, the deflection point 414 of each strut can be positioned at any location along the length of the strut 408. For example, in the illustrated embodiment, the deflection point 414 is positioned at a midpoint along the length of the strut 408 such that the first and second portions 410, 412 have equal lengths.

The degree of curvature of each portion 410, 412 of the strut 408 in plane P can be determined using Equation 1, described above with reference to prosthetic valve 300. In the illustrated embodiment, the first and second portions 410, 412 have approximately the same degree of curvature. However, in other embodiments, each portion can have a differing degree of curvature in the plane P.

Depending on the positioning of the deflection point 414 in each strut 408, in the expanded configuration the assembled frame 402 can have any of various shapes. As shown in the illustrated embodiment, the position of the deflection point 414 can give the frame 402 a non-cylindrical, tapered shape where the outflow end 406 has a greater diameter than the inflow end 404. In other embodiments, the position of the deflection point can give the frame a cylindrical shape, a frustoconical shape, a V-shape, and/or a Y-shape.

Similarly to frame 302, frame 402 can have a plurality of cells 416 arranged in a plurality of circumferentially extending rows of varying sizes. As shown in FIG. 11, the frame 402 can have five rows of cells, including a first row of cells 416*a*, a second row of cells 416*b*, a third row of cells 416*c*, a fourth row of cells 416*d*, and a fifth row of cells 416*e*. In the illustrated embodiment, row 416*a* is smaller than row 416*b*, which is smaller than center row 416*c*, and row 416*e* is smaller than row 416*d*, which is smaller than center row 416*c*.

As mentioned previously, the smaller cells, such as cells 416*a* and 416*e* in the illustrated embodiment, can mitigate bending or deformation of the frame, and the larger cells, such as cells 416*c* can allow access to the coronary vessel when the prosthetic valve 400 is implanted within the native annulus of a patient.

When compressed to the radially compressed configuration, in particular embodiments, the struts of frame 302 or 402 can elastically deform along their lengths due to the pinned connections between overlapping struts, similar to the bending of a beam supported at both ends. When the frame is retained in the radially compressed state (such as within the sheath of a delivery apparatus), the elastically deformed struts place the frame in a state of tension. Thus, when released from the radially compressed state (e.g., when deployed from the sheath of a delivery apparatus), the struts provide a spring force that causes the frame to at least partially expand. If needed, actuators (e.g., actuators 50) can be used to further expand the frame to the fully expanded state. As noted above, the struts of the frame can be formed from various metals, including plastically deformable metals, such as stainless steel or a cobalt chromium alloy, or a super-elastic material, such as a nickel titanium alloy ("NiTi"), for example Nitinol. When formed from a plastically deformable metal, the struts and the connections between the struts can be configured to maintain the struts within the range of elastic deformation for the metal as the frame is compressed from the radially expanded state to the radially compressed state (and vice versa) so as to prevent plastic deformation of the frame when transitioning between the radially compressed state and the radially expanded state.

In some embodiments, the spring force of the struts can be sufficient to produce full radial expansion of the frame from the compressed state to an expanded and operational state wherein the leaflets (e.g., leaflets 20) can function to regulate the flow of blood through the prosthetic valve. In this manner, the frame can fully self-expand from the compressed state to the expanded state without the use of actuators (e.g., actuators 50). The prosthetic valve can include one or more locking mechanisms that are configured to retain the frame in the expanded state.

The frames of prosthetic valves 300 and 400, when implanted, are configured to prevent or mitigate buckling or other deformation at the inflow end during expansion or use of the prosthetic valve. As mentioned previously, the larger cells (e.g., cells 310*c*, 416*c*) in the outflow or middle portions of the frame can allow a physician to access the coronary vessel through the outflow end of the valve by passing through the larger cells of the frame. This configuration can advantageously allow a physician to access the coronary vessel without needing to remove or displace the prior-implanted prosthetic heart valve.

As mentioned, each strut of a frame can comprise one or more apertures (e.g., apertures 312 described previously) disposed along the length of the strut. Respective hinges or junctions can be formed at the locations where struts overlap each other. At one or more locations the struts can be held together at each junction via fasteners, such as rivets or pins that extend through the apertures. The fasteners can extend through one or more apertures in the first and/or second struts to fasten the struts together while also allowing the struts to pivot relative to one another about the fastener as the frame is radially expanded or compressed. In such embodiments, a radially outer end of one or more of the fasteners can be deformed to retain the fastener within the aperture. Further details of such fasteners can be found, for example, in U.S. Publication No. 2018/0344456 and International Application No. PCT/US2020/057691, both of which are incorporated by reference herein in their entirety.

Figure 12:
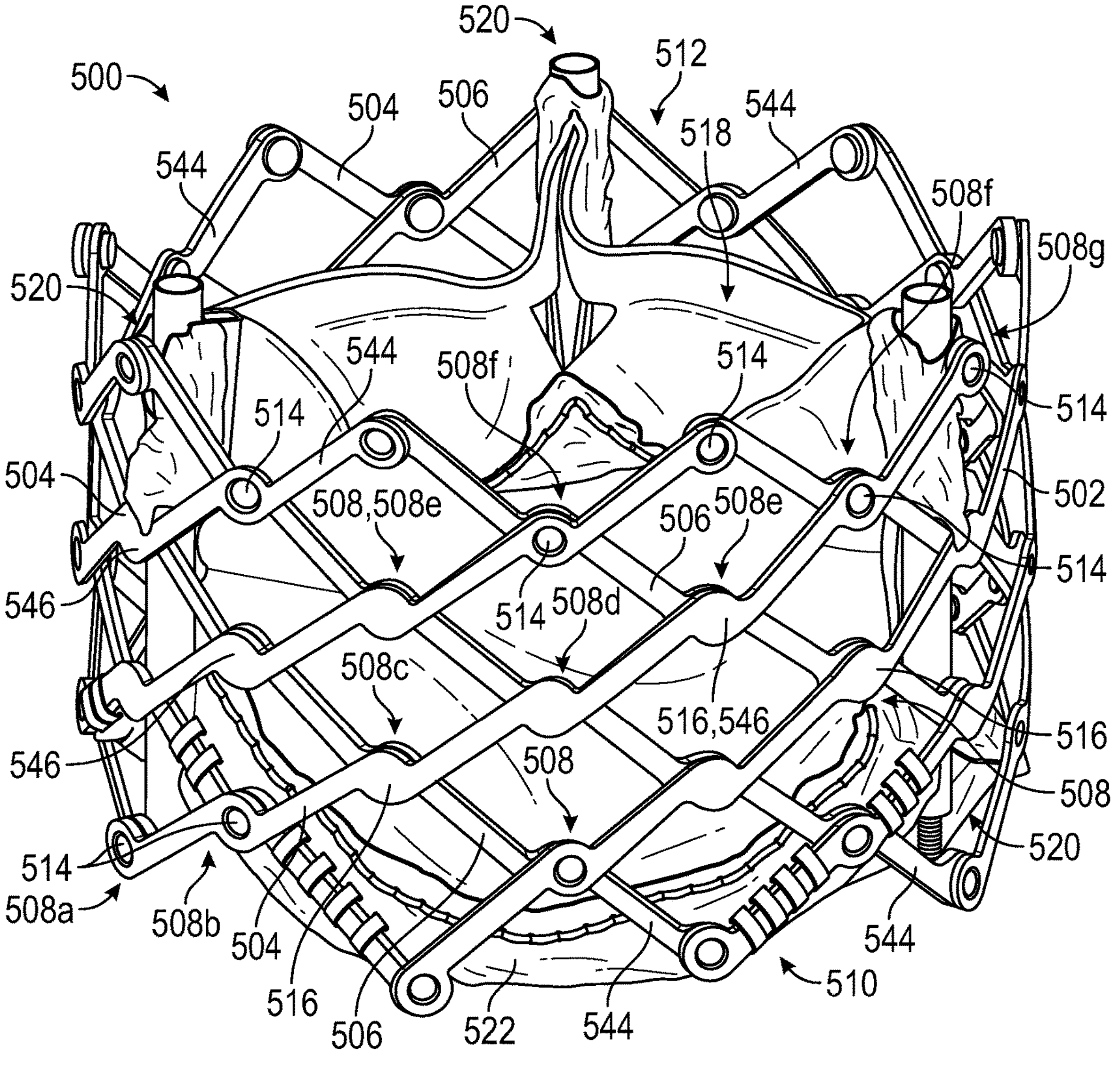
FIG. 12 is a perspective view of a prosthetic heart valve, according to one embodiment.

In some embodiments, however, each junction need not both fasten the struts to one another and allow pivotable movement of the struts relative to one another. For example, FIG. 12 illustrates a prosthetic valve 500 having a frame 502 comprising a plurality of first struts 504 (e.g., radially outer struts), each of which can be coupled to one or more struts of a plurality of second struts 506 (e.g., radially inner struts) at a plurality of junctions 508. Some junctions (e.g., one or more junctions adjacent the inflow end portion 510 of the prosthetic valve 500 and one or more junctions adjacent the outflow end portion 512) be configured as fastening junctions 514. One or more other junctions (e.g., the central junctions of a selected strut) can be configured as pivotable junctions 516 allowing the struts 504, 506 to pivot relative to one another without fastening the struts 504, 506 to one another.

For example, in the illustrated embodiment, each first strut 504 can be coupled to one or more second struts 506 via seven junctions 508*a*-508*f*. The junctions adjacent the inflow end portion 510, junctions 508*a* and 508*b*, and the junctions adjacent the outflow end portion 512, junctions 508*f* and 508*g*, can be configured as fastening junctions 514. Central junctions 508*c*-508*e* can be configured as pivotable junctions 516.

Prosthetic valve 500 can further include a valvular structure 518 disposed within the frame 502, one or more expansion and locking mechanisms 520 configured to move the prosthetic valve between a radially expanded position and a radially compressed position, and one or more skirts or sealing members (e.g., an inner skirt 522). In some embodiments, the prosthetic valve 500 can further include an outer skirt disposed on a radially outer surface of the frame.

Figure 13:
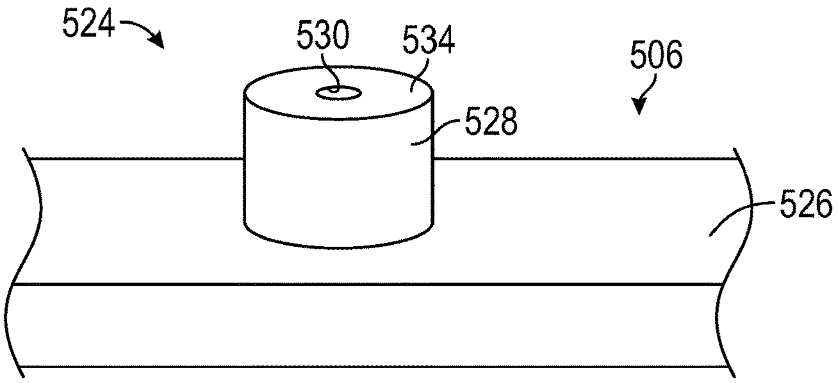
FIG. 13 is a perspective view of a portion of a strut of the prosthetic heart valve of FIG. 12.

FIG. 13 illustrates a portion of an exemplary second strut 506 (e.g., a radially inner strut) including a fastener 524 extending from a radially outer surface 526 of the strut 506. In the illustrated embodiment, the fastener 524 is integrally formed with the strut 506, however, in other embodiments, the fastener 524 can be formed separately from the strut 506 and can be coupled to the strut (e.g., using welding or other mechanically fastening means) or can be a separate component that extends through the strut 506. In the illustrated embodiment, the fastener 524 is configured as a cylindrical protrusion having a body 528 including an inner bore 530 extending therethrough. However, in other embodiments, the fastener 524 can have any of various shapes.

Figure 14:
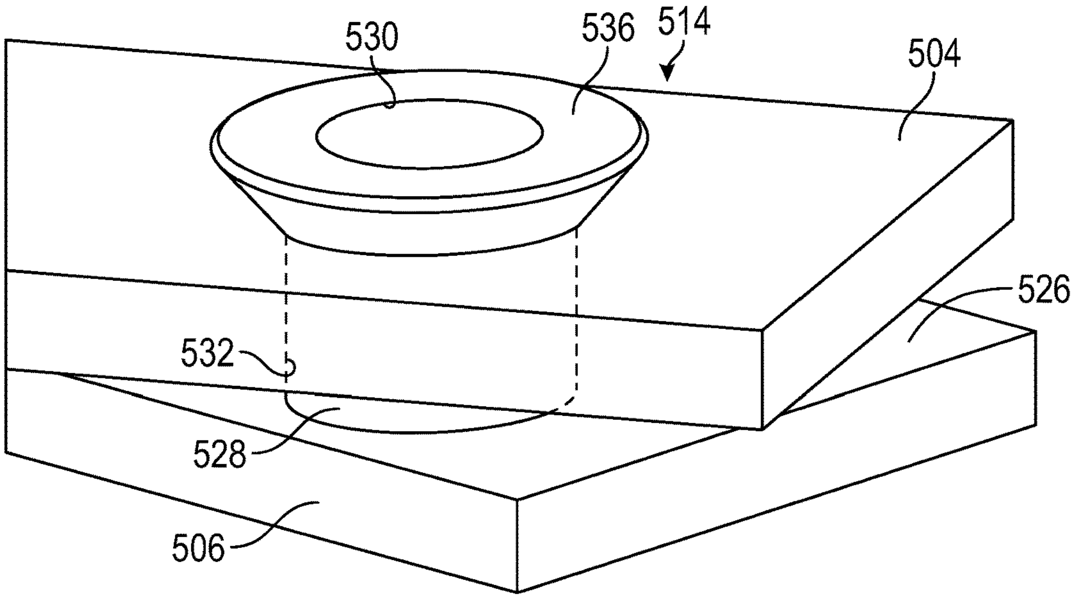
FIG. 14 is a perspective view of an exemplary fastening junction of the prosthetic heart valve of FIG. 12.

FIG. 14 illustrates an exemplary fastening junction 514 between the second strut 506 and a first strut 504 (e.g., a radially outer strut). The fastener 524 can extend through a corresponding aperture 532 in the first strut 504 and can serve as a pivot pin around which the two struts 504, 506 can pivot relative to one another. In some embodiments, an end portion 534 (FIG. 13) (e.g., a radially outer end portion) of the fastener 524 can be deformed (e.g., by applying an axially directed compressive force, such as by using a punch) to form a flanged end portion 536 having a diameter greater than that of the aperture 532, such that the fastener 524 is retained within the aperture 532 coupling the first and second struts 504, 506 to one another. The inner bore 530 of the fastener 524 can, for example, be configured to promote a uniform deformation of the end portion 534.

Figure 15:
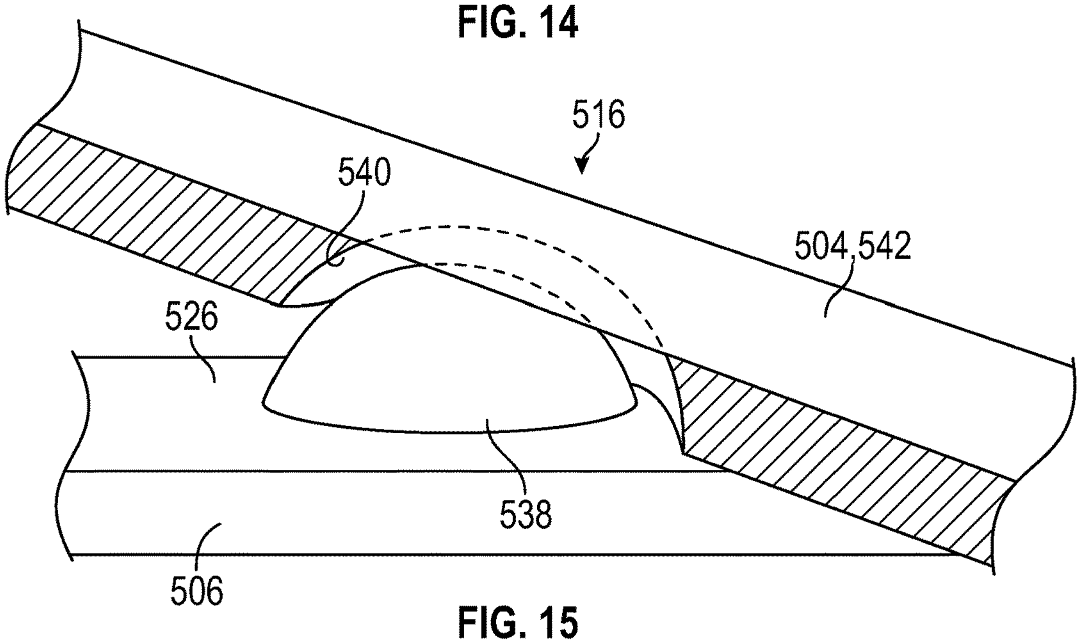
FIG. 15 is a partial cross-sectional perspective view of an exemplary pivotable junction of the prosthetic heart valve of FIG. 12.

FIG. 15 illustrates an exemplary pivotable junction 516 between a first strut 504 (e.g., a radially outer strut) and a second strut 506 (e.g., a radially inner strut), with the first strut 504 shown in cross-section along a longitudinal axis of the strut 504. The second strut 506 can comprise a protrusion 538 extending from the radially outer surface 526 of the strut 506. The first strut 504 can comprise a corresponding recess or socket 540, into which the protrusion 538 can extend. The corresponding shapes of the protrusion 538 and the socket 540 allow the first and second struts 504, 506 to pivot relative to one another about the junction 516.

In the illustrated embodiment, the protrusion 538 can have a domed, hemispherical shape, and the socket 540 can be correspondingly hemispherical. In this manner, the protrusion 538 and the socket 540 form a ball-and-socket type pivot joint. In other embodiments, the protrusion 538 can comprise various shapes and the socket 540 can have a corresponding shape configured to accept the protrusion 538 and allow rotation of the protrusion 538 within the socket 540. As shown in FIG. 15, the socket 540 can have a depth less than a thickness of the strut 504 such that the radially outer surface 542 of the first strut 504 at each pivotable junction 516 is flat.

Referring again to FIG. 12, in the illustrated embodiment, each strut 504, 506 can comprise a plurality of linear segments 544 coupled to one or more adjacent linear segments via one or more intermediate segments 546. The intermediate segments 546 of each strut 504, 506 can align with the junctions 508 at which the struts 504, 506 are coupled.

In some embodiments, each second strut 506 can comprise four fasteners 524 (FIG. 13) and three protrusions 538 spaced apart along the length of the strut 506. The fasteners 524 can be disposed such that they are aligned with junctions 508*a*, 508*b*, 508*f*, and 508*g*, and the protrusions 538 can be disposed along the strut such that they are aligned with junctions 508*c*, 508*d*, and 508*e* when the frame 502 is assembled. In such embodiments, each radially outer strut 504 can comprise four apertures 532 aligned with respective fasteners 524 at junctions 508*a*, 508*b*, 508*f*, and 508*g* and three sockets 540 aligned with the protrusions 538 at junctions 508*c*, 508*d*, and 508*e*. Such a configuration allows the struts 504, 506 to be secured to one another and pivotable relative to one another at the fastening junctions 514 and to be pivotable relative to one another at the pivotable junctions 516 without posing a risk of fasteners protruding from the pivotable junctions 516 during prosthetic valve crimping, reducing the overall crimp profile of the prosthetic valve, and/or mitigating the risk of abrasion to the native anatomy at the selected implantation site of the prosthetic valve.

In the absence of pivotable junctions such as those embodied herein, fasteners extending through apertures along the central junctions 508*c*, 508*d*, 508*e* of the frame 502 can protrude radially from the outer surface of the frame during valve crimping in an undesired manner.

Figure 16:
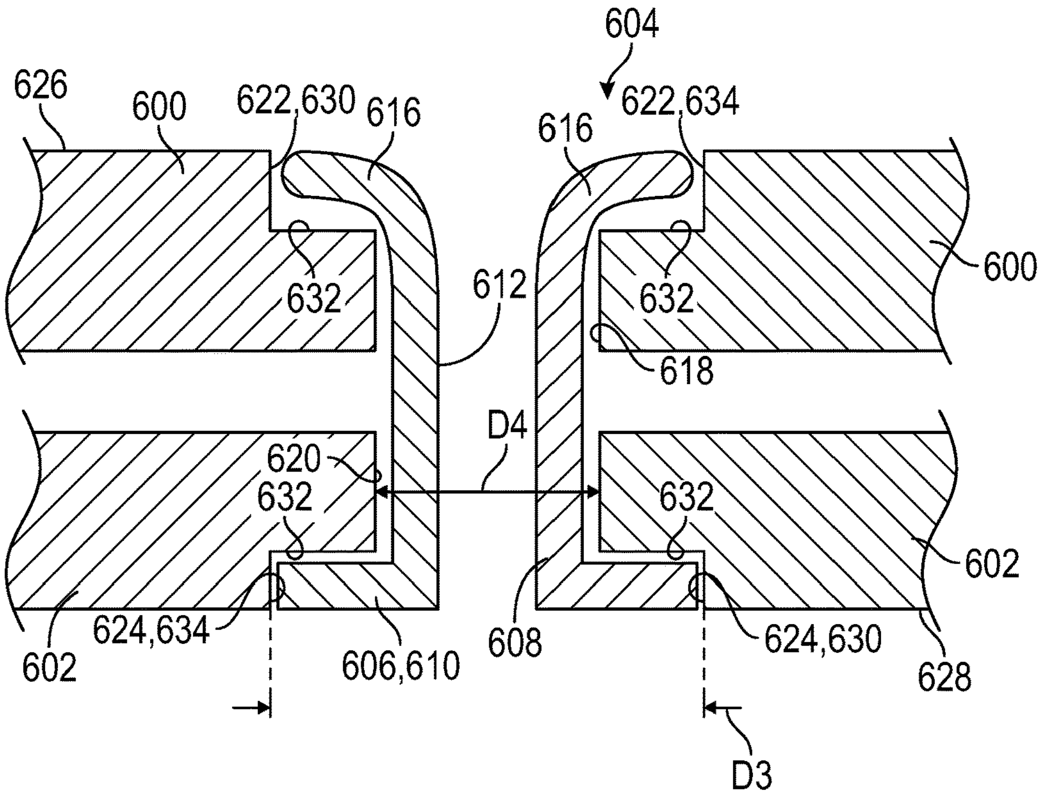
FIG. 16 is a perspective view of an exemplary fastener, according to one embodiment.

Referring to FIG. 16, in some embodiments, a prosthetic valve can comprise first and second struts 600, 602, which can be coupled to one another at an exemplary junction 604 using a fastener 606. In the embodiment shown in FIG. 16, the first strut 600 is a radially outer strut and the second strut 602 is a radially inner strut, however, in other embodiments, the first strut 600 can be a radially inner strut and the second strut 602 can be a radially outer strut.

Figure 17:
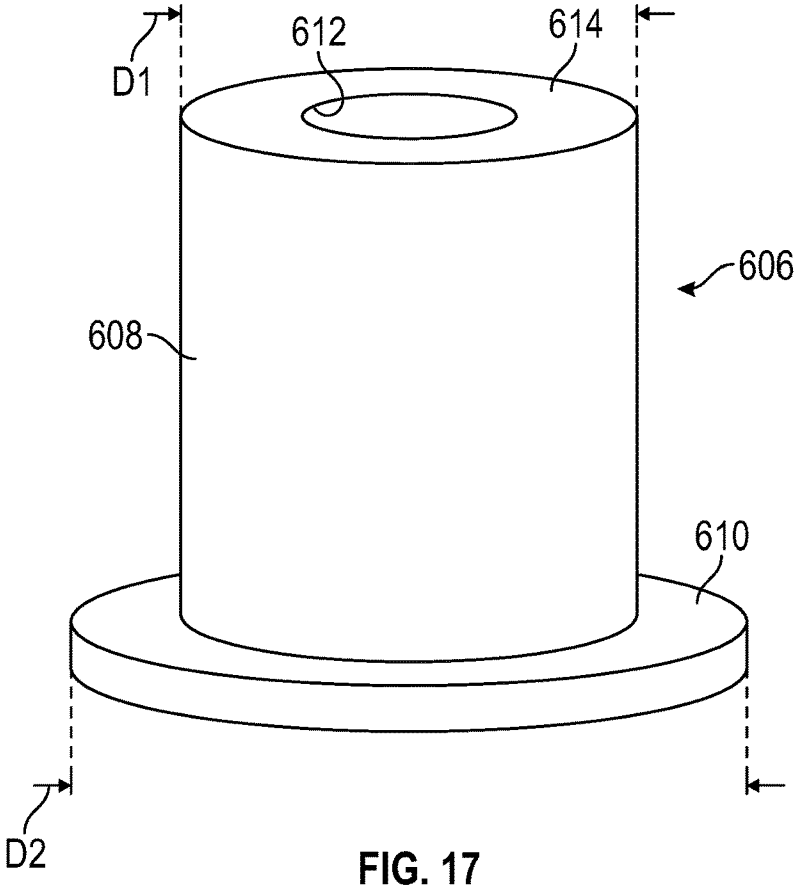
FIG. 17 is a cross-sectional side view of the fastener of FIG. 16 coupling two struts together at a junction, according to one embodiment.

As shown in FIG. 17, the fastener 606 can have a body portion 608 having a first diameter D1, a head portion 610 having a second diameter D2 greater than the first diameter D1, and an inner bore 612 extending through the body portion 608. In some embodiments, the inner bore 612 can also extend through the head portion 610. Owing to the inner bore 612, fastener 606 can, in some instances, be referred to as a "hollow" fastener. During assembly of a prosthetic valve, an end portion 614 of the fastener 606 can be deformed (e.g., by applying an axially directed compressive force such as by using a punch, etc.) to form a flanged end portion 616 (FIG. 16) having a diameter greater than that of the body portion 608. The inner bore 612 of the fastener 606 can be configured to promote a uniform deformation of the end portion 614.

As shown in FIG. 16, the first strut 600 can comprise a first aperture 618 extending through the thickness of the first strut 600, and the second strut 602 can comprise a second aperture 620 extending through the thickness of the second strut 602. In some embodiments, one or more of the apertures 618, 620 can be surrounded by a respective recess 622, 624. The first recess 622 can be disposed, for example, in the radially outer surface 626 of the first strut 600 and extend toward the inner surface of the first strut 600. The second recess 624 can be disposed in the radially inner surface 628 of the second strut 602 and extend toward the outer surface of the second strut 602.

In the illustrated embodiment of FIG. 16, each recess 622, 624 is configured as a counterbore 630. Each counterbore 630 can have a cylindrical shape including a base 632 and a side wall 634 disposed perpendicularly (or at least substantially perpendicularly) relative to one another. Each counterbore 630 can have a diameter D3 greater than a diameter D4 of the respective aperture 618, 620 such that each counterbore 630 and each aperture 618, 620 form a tiered or stepped configuration. As shown, the counterbore 630 disposed in the second strut 602 can be configured to accept the head portion 610 of the fastener 606 and the counterbore 630 disposed in the first strut 600 can be configured to accept the flanged end portion 616. Such a configuration advantageously prevents the flanged end portion 616 from protruding radially outwardly past the radially outer surface 626 of the first strut 600, thereby reducing the overall crimp profile of the prosthetic valve and mitigating the risk of abrasion to the native anatomy at the selected implantation site of the prosthetic valve.

Figure 18:
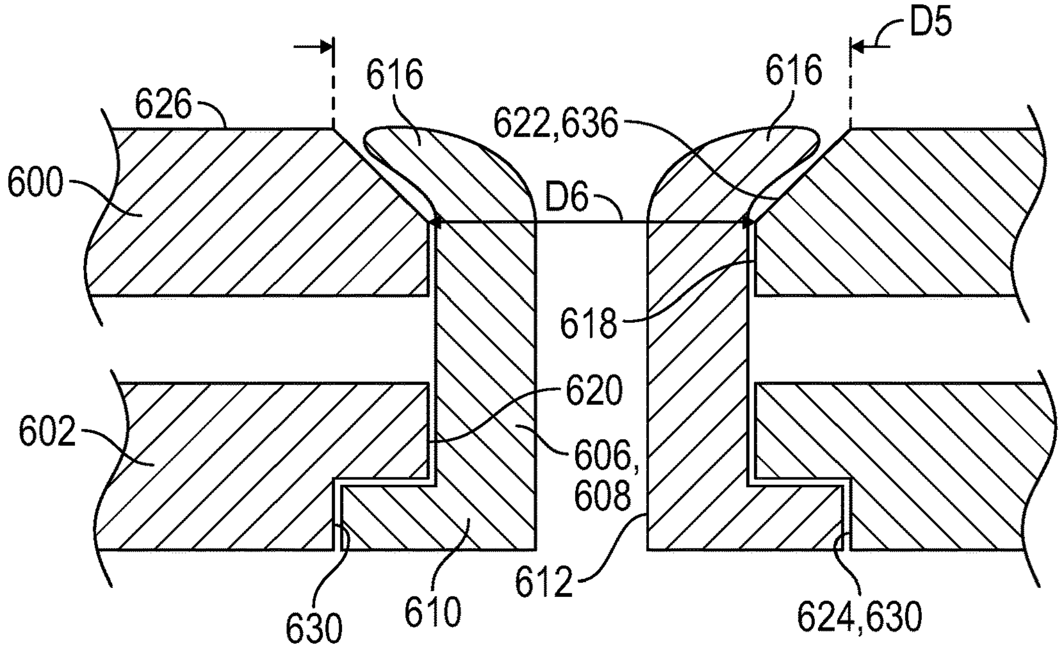
FIG. 18 is a cross-sectional side view of the fastener of FIG. 16 coupling two struts together at a junction, according to another embodiment.

Referring now to FIG. 18, in some embodiments, in lieu of a counterbore 630, the first recess 622 can be configured as a countersink 636. The countersink 636 can have a first diameter D5 at the radially outer surface 626 of the first strut 600 that tapers to a second diameter D6 where the countersink meets the aperture 618. The second diameter D6 can be substantially equal to that of the aperture 618. In other words, the countersink 636 can have a frustoconical shape. The countersink 636 can be configured to accept the flanged end portion 616 of the fastener 606 such that the flanged end portion 616 does not protrude outwardly past the radially outer surface 626 of the first strut 600. Such a configuration advantageously prevents the flanged end portion 616 from reducing the overall crimp profile of the prosthetic valve and mitigates the risk of abrasion to the native anatomy at the selected implantation site of the prosthetic valve.

In other embodiments, both recesses 622, 624, can be configured as countersinks 636. In still other embodiments, the second recess 624 can be configured as a countersink 636 and the first recess 622 can be configured as a counterbore 630, or vice versa.

Figure 19:
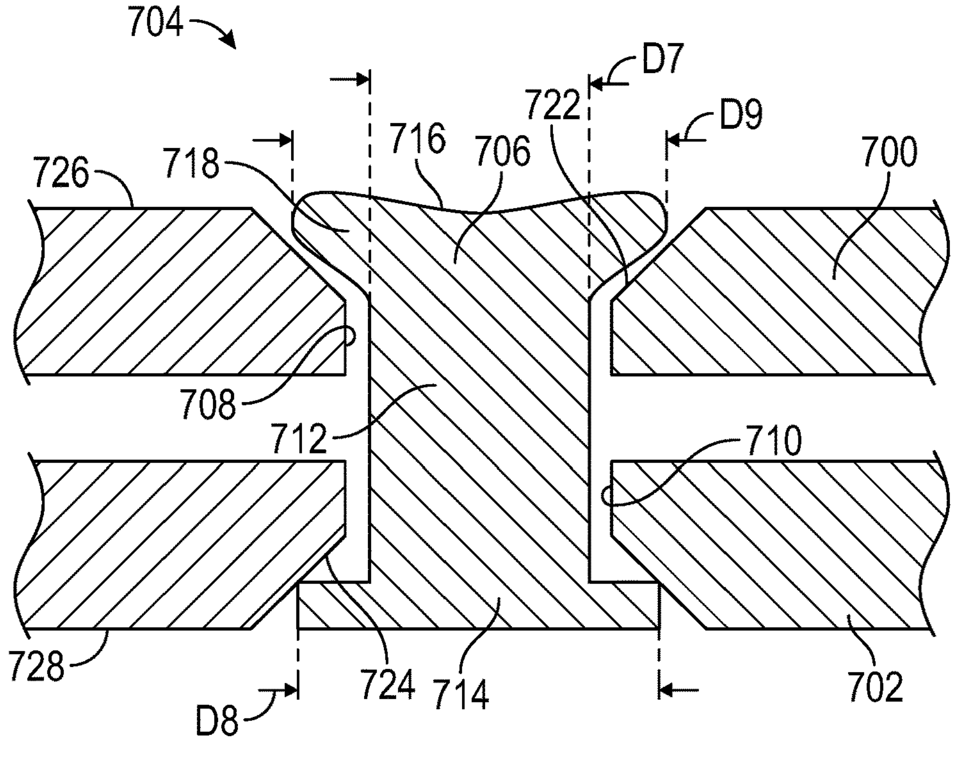
FIG. 19 is a cross-sectional side view of another embodiment of a fastener coupling two struts together at a junction.
Figure 20:
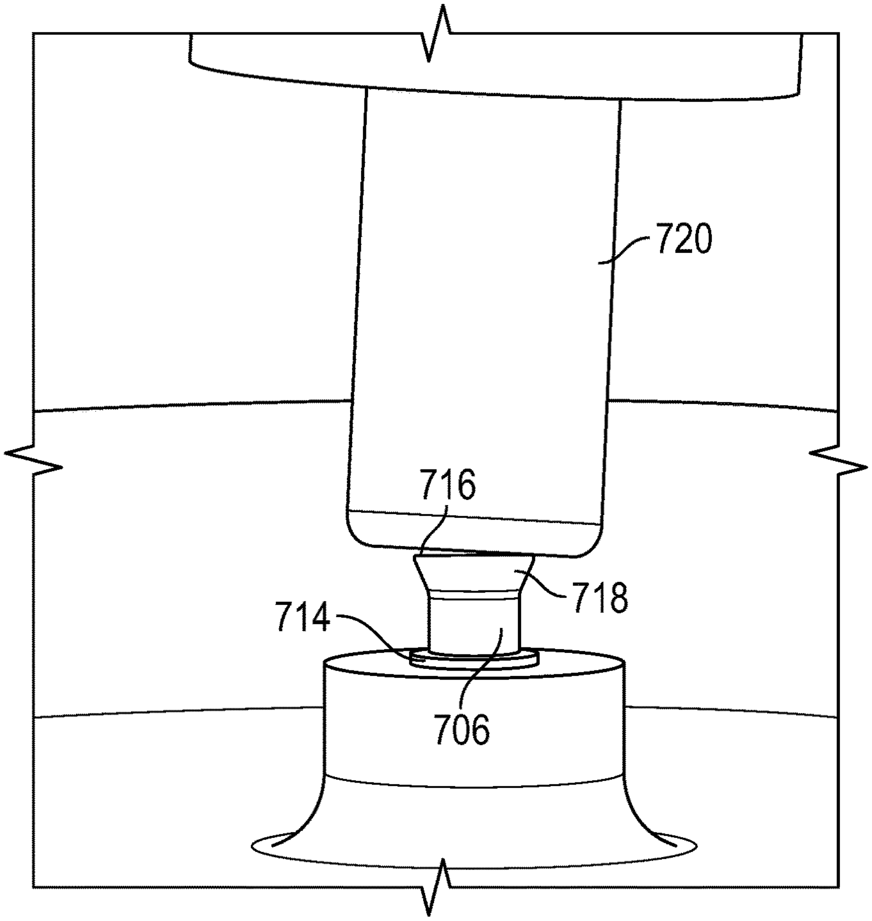
FIG. 20 is a side elevational view of a fastener during the process of radial riveting using a riveting member.

Referring now to FIGS. 19-20, in another embodiment, a prosthetic heart valve can comprise first and second struts 700, 702 coupled together at an exemplary junction 704 using a fastener 706 extending through apertures 708, 710 in the first and second struts 700, 702. In the embodiment shown in FIG. 19, the first strut 700 is a radially outer strut and the second strut 702 is a radially inner strut, however, in other embodiments, the first strut can be a radially inner strut and the second strut can be a radially outer strut.

The fastener 706 can have a body portion 712 having a first diameter D7 and a head portion 714 having a second diameter D8 greater than the first diameter D7. Due to the lack of an inner bore, fastener 706 can be referred to as a "full matter" pin or fastener. During assembly of a prosthetic valve, an end portion 716 of the fastener 706 can be deformed (e.g., using radial riveting) to form a flanged end portion 718 having a diameter D9 greater than a diameter of the apertures 708, 710. Accordingly, the fastener 706 is retained within the apertures 708, 710 on the radially inner end by head portion 714 and on the radially outer end by flanged end portion 718, thereby coupling the first and second struts 700, 702 to one another and providing a pivot pin about which the struts 700, 702 can pivot relative to one another.

Referring to FIG. 20, in some embodiments, the fastener 706 can be deformed using radial riveting. Radial riveting can be performed using a riveting member 720. The riveting member 720 can rotate around the fastener 706, applying pressure to the radially outer end surface 716 in a rosette shaped path (e.g., a hypocycloid path) to gently deform the fastener 706, thereby forming the flanged portion 718. The longitudinal axis of the riveting member 720 is disposed at an angle relative to the riveting surface (e.g., the radially outer end surface 716 of the fastener 706). The amount of applied force, the length of the riveting process, and the shape of the riveting member 720 can each be modified in order to vary the diameter, thickness, and/or shape of the flanged portion 718.

Radial riveting has various advantages. Namely, radial riveting applies very little lateral force, mitigating the need to clamp or fix the struts 700, 702 in place during the riveting process, and applies very little axial force, thereby mitigating the risk of damaging or bending the struts 700, 702. Moreover, since radial riveting is a cold-forming process, the flanged portion 718 can be formed without deforming or swelling the remainder of the fastener body 712. The radial riveting process can further produce a smooth, finished surface on the flanged end portion 718, mitigating potential damage if the fastener 706 comes in contact with the sheath of the delivery apparatus during delivery of the prosthetic valve and/or comes in contact with the native anatomy of the implantation site. This configuration can advantageously simplify assembly of a prosthetic valve, for example, by allowing much simpler processing and machining procedures to be used. This configuration further avoids impact punching, such as is performed on hollow tube fasteners having internal bores. Drilling internal bores can be difficult when components are very small, and internal bores can weaken the components. As such, larger components (e.g., pins) are needed. Full matter fasteners do not have an internal bore, and therefore, the diameter of full matter fasteners (e.g., the fastener 706) can be smaller than that of typical hollow fasteners.

Referring again to FIG. 19, each strut 700, 702 can include a respective recess 722, 724 surrounding the aperture 708, 710. Each recess 722, 724 can be configured as a counterbore or countersink and can be configured to receive the head portion 714 or the flanged end portion 718 of the fastener 706. The first recess 722 can be disposed, for example, in the radially outer surface 726 of the first strut 700 and the second recess 722 can be disposed in the radially inner surface 728 of the second strut 702. In the illustrated embodiment, both the first and second recess 722, 724 are configured as countersinks, similar to countersink 636 described previously. In other embodiments, both recesses 722, 724 can be configured as counterbores (e.g., similar to counterbores 630 described previously), in still other embodiments, the first recess 722 can be a counterbore and the second recess 724 can be a countersink, or vice versa.

Figure 21:
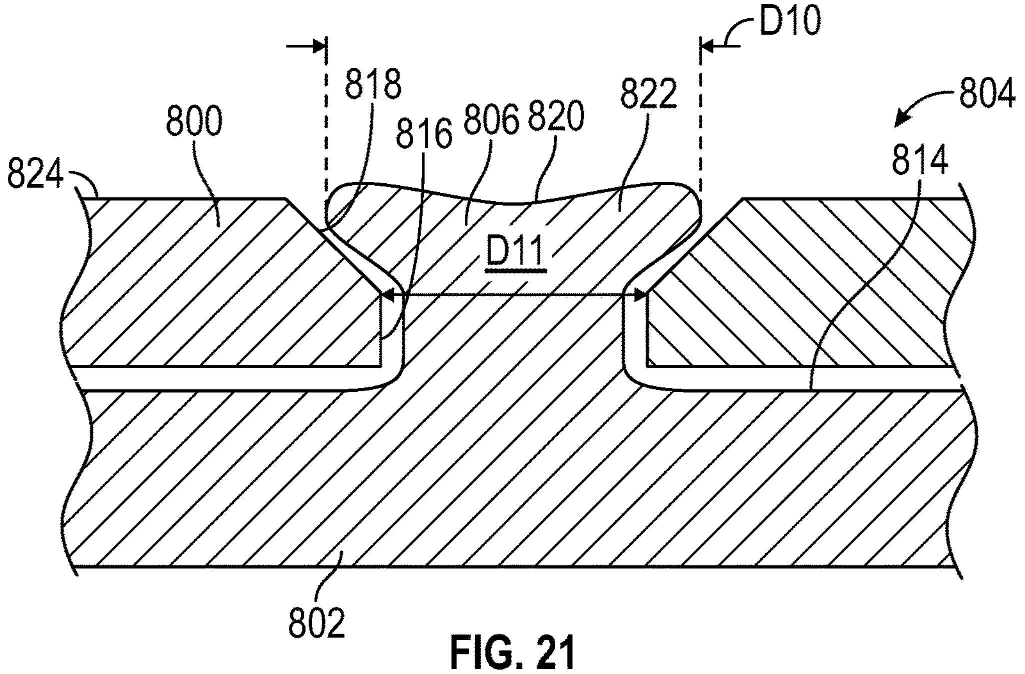
FIG. 21 is a cross-sectional side view of a fastener coupling two struts together at a junction after the radial riveting process.
Figure 22:
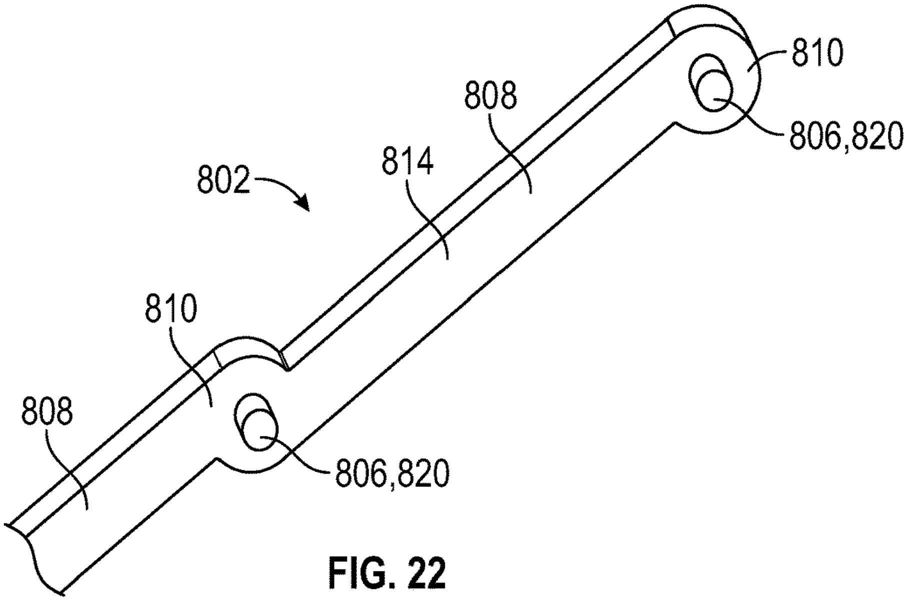
FIG. 22 is a perspective view of a portion of a strut, according to one embodiment.

Referring to FIGS. 21-22, in some embodiments, in lieu of separately formed fasteners such as fasteners 606 and 706 described previously, a prosthetic valve can comprise first and second struts 800, 802 coupled together at a junction 804 via a fastener 806 formed integrally with the second strut 802. In the embodiment shown in FIG. 21, the first strut 800 is a radially outer strut and the second strut 802 is a radially inner strut, however, in other embodiments, the first strut can be a radially inner strut and the second strut can be a radially outer strut.

As shown in FIG. 22, the second strut 802 can comprise a plurality of linear segments 808 coupled together via a plurality of intermediate portions 810. Each intermediate portion 810 can include an integrally-formed fastener 806 extending from a surface 814 (e.g., a radially outer surface) of the strut 802. As shown, the integrally-formed fasteners 806 can be full-matter fasteners lacking an inner bore. Due to the absence of an inner bore, fasteners 806 can have a relatively small diameter when compared to the diameter of hollow fasteners, such as fasteners 606. Accordingly, in such embodiments, the intermediate portions 810 of the struts 800, 802 can be correspondingly narrower. Such a configuration advantageously allows a prosthetic valve including such struts 800, 802 to have a smaller diameter when in the compressed configuration.

During assembly of the prosthetic valve, each fastener 806 can be inserted through a corresponding aperture 816 in a respective first strut 800 (e.g., a radially outer strut), as shown in FIG. 21. The aperture 816 can be surrounded by a recess 818 disposed in a radially outer surface 824 of the first strut 800. In the illustrated embodiment, recess 818 is configured as a countersink (similar to countersink 636), however, in other embodiments, recess 818 can be configured as a counterbore (similar to counterbore 630). After insertion of the fastener 806 through the aperture 816, a end portion 820 of the fastener 806 can be deformed (e.g., using radial riveting) to form a flanged end portion 822 having a diameter D10 greater than a diameter D11 of the aperture 816, such that fastener 806 is retained within the aperture 816, thereby coupling the first and second struts 800, 802 to one another and providing a pivot pin about which the struts 800, 802 can pivot relative to one another.

Figure 23:
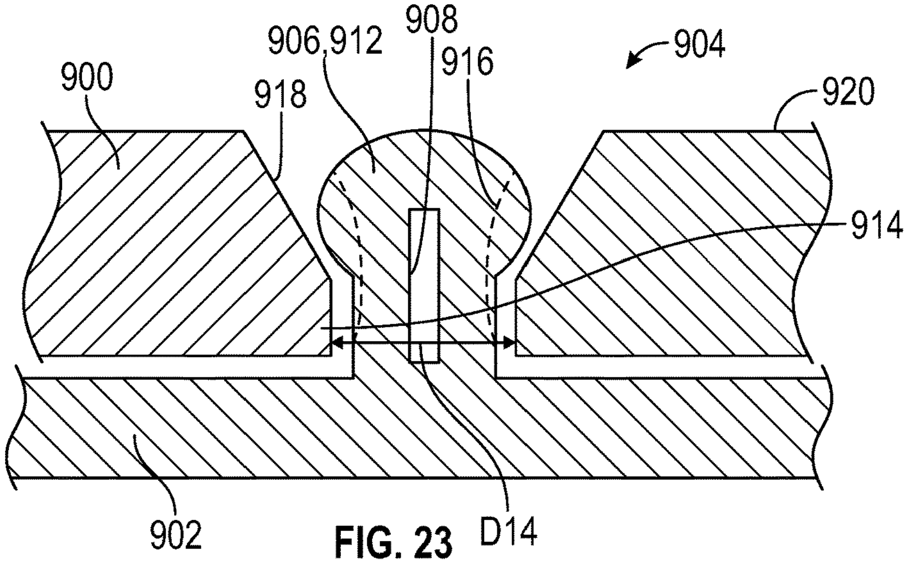
FIG. 23 is a cross-sectional side elevation view of a fastener extending from a strut, according to one embodiment.
Figure 24:
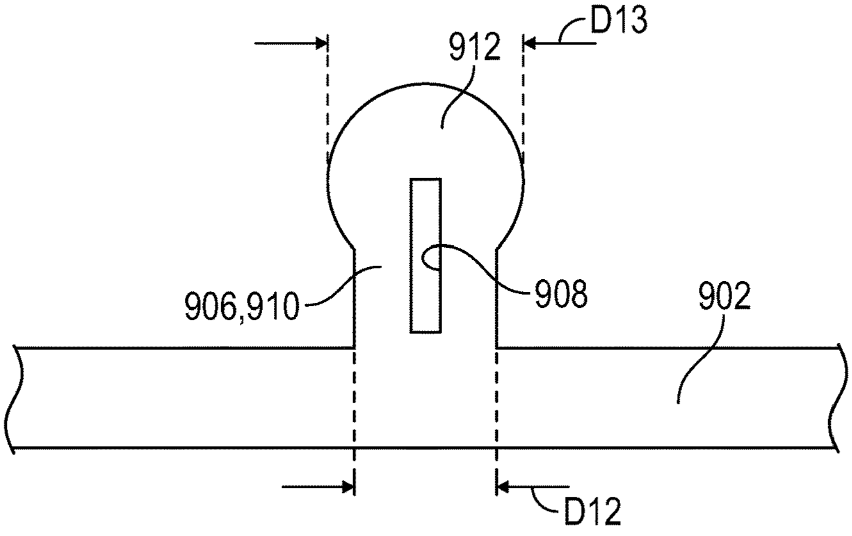
FIG. 24 is a cross-sectional side elevation view of the fastener of FIG. 23 used to couple two struts together at a junction.

Referring now to FIGS. 23-24, in some embodiments, a prosthetic valve can comprise first and second struts 900, 902 coupled together at an exemplary junction 904 via a fastener 906 including an inner slot 908. In the illustrated embodiment, fastener 906 is formed integrally with second strut 902. However, in other embodiments, fastener 906 can be formed integrally with first strut 900 or can be formed separately from both the first and second struts 900, 902 and can be coupled thereto by a head portion (e.g., such as head portion 714 of fastener 706) formed at the base of the fastener 906.

Referring to FIG. 24, the fastener 906 can comprise a body portion 910 having a first diameter D12 and a head portion or protrusion 912 configured as a flared or bulging portion having a second diameter D13 greater than the first diameter D12. As mentioned, the fastener 906 can comprise an inner slot 908 extending at least partially along the length of the fastener 906. In some embodiments, the slot 908 can extend through a thickness of the fastener 906 such that the slot divides the fastener 906 into two halves. In such embodiments, the two halves may be referred to as "ears" or "tabs." In other embodiments (and as depicted in FIGS. 23-24), the slot 908 can be fully enclosed within the fastener 906, thereby forming a hollow lumen extending through the fastener. In such instances, the inner slot may be referred to as "a window."

The fastener 906 can comprise a resilient material configured to allow the fastener 906 to be squeezed or compressed such that the slot 908 can narrow and then resiliently return to its unnarrowed state, such that the fastener 906 can move between a compressed configuration and an uncompressed configuration. For example, the fastener 906 can comprise stainless steel, cobalt chromium alloy, nickel titanium alloy ("NiTi" or "Nitinol") and/or other elastically deformable materials (including polymers).

Referring again to FIG. 23, during assembly of the prosthetic valve, the fastener 906 can be inserted through an aperture 914 in the first strut 900 (e.g., a radially outer strut). The aperture 914 can have a diameter D14 narrower than the diameter D13 of the protrusion 912. Accordingly, the fastener 906 can be compressed as it is forced through the aperture 914 such that the protrusion 912 deforms axially inwardly (as represented by dotted lines 916), narrowing the inner slot 908. Once the protrusion 912 emerges from the aperture 914 it can resiliently return to its original shape having a diameter D13 greater than the diameter D14 of the aperture, retaining the fastener 906 within the aperture 914 and thereby coupling the first and second struts 900, 902 to one another and providing a pivot pin about which the struts 900, 902 can pivot relative to one another.

As shown in FIG. 23, the aperture 922 can be surrounded by a recess 918. In the illustrated embodiment, recess 918 is configured as a countersink (similar to countersink 636) having a tapered shape that flares from a first diameter at the aperture to a second, larger diameter at the radially outer surface 920 of the first strut 900, however, in other embodiments, recess 918 can be configured as a counterbore (similar to counterbore 630). The recess 918 can be configured such that the protrusion 912 can be disposed within the recess 918 without extending past the radially outer surface 920 of the first strut 900.

Such a configuration allows each second strut 902 to be preformed with a plurality of fasteners 906 each formed with a protrusion 912. This advantageously allows the frame of the prosthetic valve to be assembled from struts 900, 902 by simply inserting the fasteners 906 through apertures 914 in the first struts 900. No additional steps (e.g., flanging the fasteners via riveting or punching) or specific tools (e.g., punch or riveting member) are required to retain the fasteners 906 within the apertures 914.

Additional Examples of the Disclosed Technology

In view of the above described implementations of the disclosed subject matter, this application discloses the additional examples enumerate below. It should be noted that one feature of an example in isolation or more than one feature of the example taken in combination and, optionally, in combination with one or more features of one or more further examples are further examples also falling within the disclosure of this application.

Example 1. An implantable prosthetic device, comprising a frame that is radially expandable and compressible between a radially compressed configuration and a radially expanded configuration. The frame comprises a plurality of struts, each strut comprising a first portion and a second portion separated by a deflection point. Each strut is curved helically with respect to a first, longitudinal axis of the frame. The first portion of each strut is curved in a first direction with respect to a first line parallel to a second axis that is perpendicular to the first, longitudinal axis of the frame. The second portion of each strut is curved in a second direction with respect to a second line parallel to the second axis.

Example 2. The implantable prosthetic device of any example herein, particularly example 1, wherein the first portion of the strut is convex with respect to an outflow end of the frame.

Example 3. The implantable prosthetic device of any example herein, particularly any one of examples 1-2, wherein the second portion of the strut is concave with respect to an outflow end of the frame.

Example 4. The implantable prosthetic device of any example herein, particularly any one of examples 1-3, wherein the first portion of the strut is positioned adjacent an inflow end of the frame and the second portion is positioned adjacent an outflow end of the frame.

Example 5. The implantable prosthetic device of any example herein, particularly any one of examples 1-3, wherein the first portion of the strut is positioned adjacent an outflow end of the frame and the second portion is positioned adjacent an inflow end of the frame.

Example 6. The implantable prosthetic device of any example herein, particularly any one of examples 1-5, wherein the first and second portions have equal lengths.

Example 7. The implantable prosthetic device of any example herein, particularly any one of examples 1-5, wherein the first portion has a first length and the second portion has a second length, and wherein the first length is greater than the second length.

Example 8. The implantable prosthetic device of any example herein, particularly any one of examples 1-5, wherein the first portion has a first length and the second portion has a second length, and wherein the second length is greater than the first length.

Example 9. The implantable prosthetic device of any example herein, particularly any one of examples 1-8, wherein the plurality of struts comprises a first set of a plurality of struts extending in a first direction and a second set of a plurality of struts extending in a second direction, and wherein each strut of the first set of struts is connected to at least one strut of the second set of struts to form a plurality of cells.

Example 10. The implantable prosthetic device of any example herein, particularly example 9, wherein the plurality of cells comprises a first row of cells adjacent a first end of the frame, and a second row of cells disposed between the first end and a second end of the frame, the first row of cells being smaller than the second row of cells.

Example 11. The implantable prosthetic device of any example herein, particularly example 10, further comprising a third row of cells adjacent the second end of the frame, the third row of cells being smaller than the second row of cells.

Example 12. The implantable prosthetic device of any example herein, particularly any one of examples 1-11, wherein each strut extends from a first end of the frame to an axially opposed second end of the frame.

Example 13. The implantable prosthetic device of any example herein, particularly any one of examples 1-12, wherein when the frame is in the radially expanded configuration the frame tapers from a first diameter at a first location on the frame to a second diameter at a second location on the frame axially spaced from the first location, the first diameter being greater than the second diameter.

Example 14. The implantable prosthetic device of any example herein, particularly any one of examples 1-12, wherein when the frame is in the radially expanded configuration the frame has a first diameter at a first location on the frame and a second diameter at a second location on the frame axially spaced from the first location, the first and second diameters being substantially equal such that the frame has a cylindrical shape.

Example 15. The implantable prosthetic device of any example herein, particularly any one of examples 1-14, further comprising a valve assembly comprising a plurality of leaflets mounted inside the frame.

Example 16. The implantable prosthetic device of any example herein, particularly any one of examples 1-15, wherein the plurality of struts comprises a plurality of inner struts and a plurality of outer struts pivotably coupled to the inner struts at a plurality of pivot joints.

Example 17. An implantable prosthetic device, comprising a frame having first and second opposing axial ends. The frame comprises a plurality of inner and outer struts pivotably coupled to one another at a plurality of junctions. Each strut has a first portion and a second portion, the first portion forming a convex curve facing the first end of the frame and the second portion forming a concave curve facing the first end of the frame.

Example 18. The implantable prosthetic device of any example herein, particularly example 17, wherein a projection of each strut in a plane parallel to a longitudinal axis of the frame is curved.

Example 19. The implantable prosthetic device of any example herein, particularly any one of examples 17-18, wherein the first and second portions each comprise a plurality of segments, wherein each segment of the first portion is offset from each adjacent segment in a first direction such that the first portion is curved along a length of the first portion, and wherein each segment of the second portion is offset from each adjacent segment in a second direction such that the second portion is curved along a length of the second portion.

Example 20. An implantable prosthetic device comprising a radially expandable and compressible frame having an inflow end portion and an outflow end portion. The frame comprises a plurality of first struts extending in a first direction, and a plurality of second struts extending in a second direction and coupled to the first plurality of struts at a plurality of junctions. A first set of selected junctions being configured as fastening junctions and a second set of selected junctions being configured as pivotable junctions. Each fastening junction comprises a fastener configured to couple a respective first strut and second strut to one another such that the respective first and second struts can pivot relative to one another about the fastener. Each pivotable junction comprises a protrusion extending from a surface of a respective second strut, the protrusion disposed within a corresponding recess in a surface of a respective first strut such that the respective first and second struts can pivot relative to one another about the protrusion.

Example 21. The implantable device any example herein, particularly example 20, wherein the plurality of second struts is disposed radially inwardly of the plurality of first struts.

Example 22. The implantable device of any example herein, particularly any one of examples 20-21, wherein each strut comprises a plurality of linear segments coupled to one or more adjacent linear segments via one or more intermediate segments.

Example 23. The implantable device of any example herein, particularly any one of examples 20-22, wherein a respective first strut is coupled to one or more second struts via first and second fastening junctions adjacent the inflow end of the frame and third and fourth fastening junctions adjacent the outflow end of the frame.

Example 24. The implantable device of any example herein, particularly any one of examples 20-23, wherein a respective first strut is coupled to one or more second struts via seven junctions, and wherein four junctions are fastening junctions and three junctions are pivotable junctions.

Example 25. The implantable device of any example herein, particularly any one of examples 20-24, wherein each first strut comprises one or more apertures extending through a thickness of the strut and one or more recessed portions having a domed shape.

Example 26. The implantable device of any example herein, particularly any one of examples 20-25, wherein each second strut comprises one or more fasteners extending from a surface of the strut and one or more protrusions extending from the surface of the strut.

Example 27. The implantable device of any example herein, particularly any one of examples 20-26, wherein each protrusion has a hemispherical shape.

Example 28. The implantable device of any example herein, particularly any one of examples 20-27, wherein each fastener has a cylindrical shape having a flanged end portion.

Example 29. The implantable device of any example herein, particularly any one of examples 20-28, wherein each fastener further comprises an inner bore.

Example 30. The implantable device of any example herein, particularly any one of examples 20-29, wherein each fastener and each protrusion are disposed at a respective intermediate segment.

Example 31. The implantable device of any example herein, particularly any one of examples 20-30, wherein the fasteners are formed integrally with the second struts.

Example 32. The implantable device of any example herein, particularly any one of examples 20-31, wherein the protrusions are formed integrally with the second struts.

Example 33. The implantable device of any example herein, particularly any one of examples 20-32, wherein each second strut comprises a plurality of segments coupled to one or more adjacent segments via one or more intermediate segments and wherein each intermediate segment includes at least one of an aperture extending through a thickness of the strut and a protrusion extending from a surface of the strut.

Example 34. The implantable device of any example herein, particularly any one of examples 20-33, wherein each strut extends from a first end of the frame to an axially opposed second end of the frame.

Example 35. The implantable device of any example herein, particularly any one of examples 20-34, further comprising a valvular assembly comprising a plurality of leaflets mounted inside the frame.

Example 36. An implantable prosthetic device comprising a radially expandable and compressible frame having an inflow end portion and an outflow end portion. The frame comprises a plurality of first struts extending in a first direction, each first strut comprising a plurality of linear segments coupled to one or more adjacent linear segments via one or more intermediate segments. Each first strut comprises at least one aperture extending through a thickness of the first strut at an intermediate segment and at least one recess extending into the thickness of the first strut at an additional intermediate segment. The frame further comprises a plurality of second struts extending in a second direction and coupled to the plurality of first struts at a plurality of junctions. Each second strut comprises a plurality of linear segments coupled to one or more adjacent linear segments via one or more intermediate segments. Each second strut comprises at least one fastener extending from a surface of the strut at an intermediate segment and at least one protrusion extending from the surface of the strut at an additional intermediate segment. Selected junctions of the plurality of junctions are configured as fastening junctions and selected junctions are configured as pivotable junctions.

Example 37. The implantable device of any example herein, particularly example 36, wherein at each fastening junction a respective fastener of a respective second strut extends through a respective aperture of a respective first strut to couple the first and second struts to one another such that the first and second struts can pivot relative to one another about the fastener.

Example 38. The implantable device of any example herein, particularly any one of examples 36-37, wherein at each pivotable junction a respective protrusion of a respective second strut is disposed within a respective recess of a respective first strut such that the first and second struts can pivot relative to one another about the protrusion.

Example 39. The implantable device of any example herein, particularly any one of examples 36-38, wherein the plurality of second struts is disposed radially inwardly of the plurality of first struts.

Example 40. The implantable device of any example herein, particularly any one of examples 36-38, wherein a respective first strut is coupled to one or more second struts via first and second fastening junctions adjacent the inflow end of the frame and third and fourth fastening junctions adjacent the outflow end of the frame.

Example 41. The implantable device of any example herein, particularly any one of examples 36-40, wherein a respective first strut of is coupled to one or more second struts via seven junctions, and wherein four junctions are fastening junctions and three junctions are pivotable junctions.

Example 42. The implantable device of any example herein, particularly any one of examples 36-41, wherein each recess has a hemispherical shape.

Example 43. The implantable device of any example herein, particularly any one of examples 36-42, wherein each protrusion has a hemispherical shape.

Example 44. The implantable device of any example herein, particularly any one of examples 36-43, wherein each fastener has a cylindrical shape having a flanged end portion.

Example 45. The implantable device of any example herein, particularly any one of examples 36-44, wherein each fastener further comprises an inner bore.

Example 46. The implantable device of any example herein, particularly any one of examples 36-45, wherein the fasteners and protrusions are formed integrally with the second struts.

Example 47. The implantable device of any example herein, particularly any one of examples 36-46, wherein each strut extends from a first end of the frame to an axially opposed second end of the frame.

Example 48. The implantable device of any example herein, particularly any one of examples 36-47, further comprising a valve assembly comprising a plurality of leaflets mounted inside the frame.

Example 49. An implantable prosthetic device comprising a radially expandable and compressible frame having an inflow end portion and an outflow end portion. The frame comprises a plurality of first struts extending in a first direction, each first strut comprises at least one first aperture extending through a thickness of the first strut and a first recess disposed around the first aperture. The frame further comprises a plurality of second struts extending in a second direction, each second strut comprises at least one second aperture extending through a thickness of the second strut and a second recess disposed around the second aperture. The frame further comprises a plurality of fasteners, each fastener extending through a respective first aperture and a respective second aperture to couple respective first and second struts to one another at a junction. Each fastener comprising a body portion, a head portion sized to retain the fastener within the second recess and a flanged end portion sized to retain the fastener within the first recess.

Example 50. The implantable device any example herein, particularly example 49, wherein each fastener comprises an inner bore extending along at least a portion of a length of the fastener.

Example 51. The implantable device of any example herein, particularly any one of examples 49-50, wherein each flanged end portion is formed using a punch member to apply force to a first aperture of the inner bore to plastically deform the flanged end portion.

Example 52. The implantable device of any example herein, particularly example 49, wherein each fastener is a solid piece of material.

Example 53. The implantable device of any example herein, particularly example 52, wherein each flanged end portion is formed by radial riveting.

Example 54. The implantable device of any example herein, particularly any one of examples 49-53, wherein the first recess is sized such that the flanged end portion does not extend past a radially outer surface of the first strut.

Example 55. A method comprising inserting a fastener through a first aperture in a first strut and a second aperture in a second strut, the fastener comprising a body portion having a first diameter, a head portion having a second diameter larger than the first diameter, and an end portion. The method further comprises disposing the head portion of the fastener in a recess surrounding the second aperture, the recess disposed in a radially inner surface of the second strut, and deforming the end portion of the fastener to form a flanged head portion disposed in an additional recess surrounding the first aperture to couple the first and second struts to one another such that the first and second struts can pivot relative to one another about the fastener.

Example 56. The method of any example herein, particularly example 55, wherein the fastener comprises an inner bore extending at least partially along a length of the fastener, and wherein deforming the end portion of the fastener comprises using a punch member to apply force to the end portion to deform the end portion from a first diameter to a second diameter larger than the first diameter.

Example 57. The method of any example herein, particularly example 55, wherein deforming the end portion of the fastener comprises radially riveting the end portion to deform the end portion from a first diameter to a second diameter larger than the first diameter.

Example 58. An implantable prosthetic device comprising a radially expandable and compressible frame having an inflow end portion and an outflow end portion. The frame comprises a plurality of first struts extending in a first direction, each first strut comprises at least one aperture extending through a thickness of the first strut and a recess disposed around the aperture. The frame further comprises a plurality of second struts extending in a second direction, each second strut comprises at least one fastener extending from a surface of the second strut, each fastener extending through a respective aperture to couple respective first and second struts to one another at a junction. Each fastener comprises a body portion and a flanged end portion sized to retain the fastener within the recess.

Example 59. The implantable device of any example herein, particularly example 58, wherein each fastener comprises an inner bore extending along at least a portion of a length of the fastener.

Example 60. The implantable device of any example herein, particularly example 59, wherein each flanged end portion is formed using a punch member to apply force to a first aperture of the inner bore to plastically deform the flanged end portion.

Example 61. The implantable device of any example herein, particularly example 58, wherein each fastener is a solid piece of material.

Example 62. The implantable device of any example herein, particularly example 61, wherein each flanged end portion is formed by radial riveting.

Example 63. The implantable device of any example herein, particularly any one of examples 58-62, wherein the recess is sized such that the flanged end portion does not extend past a radially outer surface of the first strut.

Example 64. A method comprising inserting a fastener through an aperture in a first strut, the fastener extending from a radially outer surface of a second strut, and deforming an end portion of the fastener to form a flanged head portion disposed in a recess surrounding the aperture to couple the first and second struts to one another such that the first and second struts can pivot relative to one another about the fastener, the recess disposed in a radially outer surface of the first strut.

Example 65. The method of any example herein, particularly example 64, wherein the fastener comprises an inner bore extending at least partially along a length of the fastener, and wherein deforming the end portion of the fastener comprises using a punch member to apply force to the end portion to deform the end portion from a first diameter to a second diameter larger than the first diameter.

Example 66. The method of any example herein, particularly example 64, wherein deforming the end portion of the fastener comprises radially riveting the end portion to deform the end portion from a first diameter to a second diameter larger than the first diameter.

Example 67. An implantable prosthetic device comprising a radially expandable and compressible frame having an inflow end portion and an outflow end portion. The frame comprises a plurality of first struts extending in a first direction, each first strut comprises at least one aperture extending through a thickness of the first strut and a recess disposed around the aperture. The frame further comprises a plurality of second struts extending in a second direction, each second strut comprises at least one fastener extending from a surface of the second strut through a respective aperture in a first strut. Each fastener comprises a body portion, a protrusion, and an inner slot extending at least partially along a length of the fastener, the fastener being movable between a compressed configuration and an uncompressed configuration. When in the uncompressed configuration the protrusion is sized to retain the fastener within the respective aperture to couple the first and second struts to one another and allow the first and second struts to pivot relative to one another about the fastener.

Example 68. The implantable device of any example herein, particularly example 67, wherein the protrusion is disposed within the recess such that the protrusion does not extend past a radially outer surface of the first strut.

Example 69. The implantable device of any example herein, particularly any one of examples 67-68, wherein when in the uncompressed configuration the protrusion has a diameter greater than that of the body portion and the aperture.

Example 70. A method comprising forcing a fastener against an aperture in a first strut, the fastener extending from a radially outer surface of a second strut and comprising a body portion, a protrusion, and an inner slot extending at least partially along a length of the fastener, the protrusion having a diameter larger than a diameter of the aperture. The method further comprises advancing the fastener through the aperture such that the fastener moves from an uncompressed configuration to a compressed configuration, and once the protrusion has emerged from a radially outer end of the aperture, allowing the fastener to resiliently expand to the uncompressed configuration such that the fastener is retained within the aperture to couple the first and second struts to one another such that the first and second struts can pivot relative to one another about the fastener.

In view of the many possible embodiments to which the principles of the disclosure may be applied, it should be recognized that the illustrated embodiments are only examples and should not be taken as limiting the scope of the disclosure or the claims. Rather, the scope of the claimed subject matter is defined by the following claims and their equivalents.

We claim:

1. An implantable prosthetic device, comprising:

a frame that is radially expandable and compressible between a radially compressed configuration and a radially expanded configuration, the frame comprising a plurality of struts, each strut of the plurality of struts extending from a first end of the frame to an axially opposed second end of the frame and comprising a first portion extending from the first end to a deflection point and a second portion extending from the deflection point to the second end, wherein each strut of the plurality of struts is curved helically with respect to a first, longitudinal axis of the frame;

wherein the first portion of each strut of the plurality of struts is curved in a first direction with respect to a first line parallel to a second axis that is perpendicular to the first, longitudinal axis of the frame;

wherein the second portion of each strut the plurality of struts is curved in a second direction with respect to a second line parallel to the second axis;

wherein each strut of the plurality of struts comprises a plurality of segments, and wherein each segment of the plurality of segments is curved;

wherein the plurality of struts comprises a first set of struts extending in a first direction and a second set of struts extending in a second direction, and wherein each strut of the first set of struts is connected to at least one strut of the second set of struts to form a plurality of cells; and wherein the plurality of cells comprises a first row of cells adjacent a first end of the frame, and a second row of cells disposed between the first end and a second end of the frame, the first row of cells being smaller than the second row of cells.

2. The implantable prosthetic device of claim 1, wherein the first portion of the strut is convex with respect to an outflow end of the frame.

3. The implantable prosthetic device of claim 1, wherein the second portion of the strut is concave with respect to an outflow end of the frame.

4. The implantable prosthetic device of claim 1, wherein the first portion of the strut is positioned adjacent an inflow end of the frame and the second portion is positioned adjacent an outflow end of the frame.

5. The implantable prosthetic device of claim 1, wherein the first portion of the strut is positioned adjacent an outflow end of the frame and the second portion is positioned adjacent an inflow end of the frame.

6. The implantable prosthetic device of claim 1, wherein the first and second portions have equal lengths.

7. The implantable prosthetic device of claim 1, wherein the first portion has a first length and the second portion has a second length, and wherein the first length is greater than the second length.

8. The implantable prosthetic device of claim 1, wherein the first portion has a first length and the second portion has a second length, and wherein the second length is greater than the first length.

9. The implantable prosthetic device of claim 1, further comprising a third row of cells adjacent the second end of the frame, the third row of cells being smaller than the second row of cells.

10. The implantable prosthetic device of claim 1, wherein when the frame is in the radially expanded configuration the frame tapers from a first diameter at a first location on the frame to a second diameter at a second location on the frame axially spaced from the first location, the first diameter being greater than the second diameter.

11. The implantable prosthetic device of claim 1, wherein when the frame is in the radially expanded configuration the frame has a first diameter at a first location on the frame and a second diameter at a second location on the frame axially spaced from the first location, the first and second diameters being substantially equal such that the frame has a cylindrical shape.

12. The implantable prosthetic device of claim 1, further comprising a valve assembly comprising a plurality of leaflets mounted inside the frame.

13. The implantable prosthetic device of claim 1, wherein each strut of the plurality of struts comprises a plurality of strut segments, wherein the plurality of struts segments comprises a first strut segment, a second strut segment and a third strut segment, the first strut segment having a first length and positioned adjacent to the deflection point, the second strut segment having a second length and positioned adjacent to an inflow end of the frame, and the third strut segment having a third length and positioned adjacent and an outflow end of the frame, wherein the first length is greater than the second length and the third length.

14. An implantable prosthetic device, comprising:

a frame that is radially expandable and compressible between a radially compressed configuration and a radially expanded configuration, the frame comprising a plurality of struts, each strut of the plurality of struts comprising a first portion and a second portion separated by a deflection point, wherein each strut of the plurality of struts is curved helically with respect to a first, longitudinal axis of the frame;

wherein the first portion of each strut of the plurality of struts is curved in a first direction with respect to a first line parallel to a second axis that is perpendicular to the first, longitudinal axis of the frame;

wherein the second portion of each strut the plurality of struts is curved in a second direction with respect to a second line parallel to the second axis;

wherein each strut of the plurality of struts comprises a plurality of segments, and wherein each segment of the plurality of segments is curved;

wherein the plurality of struts comprises a first set of struts extending in a first direction and a second set of struts extending in a second direction, and wherein each strut of the first set of struts is connected to at least one strut of the second set of struts to form a plurality of cells; wherein the plurality of cells comprises a first row of cells adjacent a first end of the frame, and a second row of cells disposed between the first end and a second end of the frame, the first row of cells being smaller than the second row of cells; and wherein the plurality of struts comprises a plurality of inner struts and a plurality of outer struts pivotably coupled to the inner struts at a plurality of pivot joints.

15. The implantable prosthetic device of claim 14, wherein each pivot joint of the plurality of pivot joints comprises a fastener extending through a first aperture of a first strut of the plurality of struts and a second aperture of a second strut of the plurality of struts.

16. The implantable prosthetic device of claim 14, wherein each pivot joint of the plurality of pivot joints comprises a protrusion formed on a first strut of the plurality of struts and a recess formed on a second strut of the plurality of struts, wherein the protrusion and the recess form a ball-and-socket type pivot joint.

17. An implantable prosthetic device, comprising:

a frame that is radially expandable and compressible between a radially compressed configuration and a radially expanded configuration, the frame comprising a plurality of struts, each strut of the plurality of struts comprising a first portion and a second portion and is curved helically with respect to a first, longitudinal axis of the frame, wherein the first portion of each strut of the plurality of struts is curved in a first direction with respect to a second axis that is perpendicular to the first, longitudinal axis of the frame, and the second portion of each strut the plurality of struts is curved in a second direction with respect to the second axis;

wherein the plurality of struts comprises a first set of struts extending in a first direction and a second set of struts extending in a second direction, and wherein each strut of the first set of struts is connected to at least one strut of the second set of struts to form a plurality of cells;

wherein the plurality of cells comprises a first row of cells adjacent a first end of the frame, and a second row of cells disposed between the first end and a second end of the frame, the first row of cells being smaller than the second row of cells; and wherein the first portion of each strut extends from a first end of the frame to a deflection point and the second portion of each strut extends from the deflection point to a second end of the frame.

* * * * *